United States Patent
Davies et al.

(10) Patent No.: US 12,240,896 B2
(45) Date of Patent: *Mar. 4, 2025

(54) GREMLIN-1 INHIBITOR FOR THE TREATMENT OF A BONE FRACTURE OR BONE DEFECT

(71) Applicant: UCB BIOPHARMA SRL, Brussels (BE)

(72) Inventors: Gareth Charles Glyndwr Davies, Slough (GB); Scott John Roberts, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 0 days.

This patent is subject to a terminal disclaimer.

(21) Appl. No.: 18/062,608

(22) Filed: Dec. 7, 2022

(65) Prior Publication Data

US 2023/0174635 A1    Jun. 8, 2023

Related U.S. Application Data

(63) Continuation of application No. 16/970,391, filed as application No. PCT/EP2019/053726 on Feb. 14, 2019, now Pat. No. 11,524,997.

(30) Foreign Application Priority Data

Feb. 15, 2018  (GB) ..................... 1802486

(51) Int. Cl.
*A61K 39/395*    (2006.01)
*A61P 19/08*    (2006.01)
*C07K 16/22*    (2006.01)

(52) U.S. Cl.
CPC .......... *C07K 16/22* (2013.01); *A61K 39/3955* (2013.01); *A61P 19/08* (2018.01); *C07K 2317/54* (2013.01); *C07K 2317/55* (2013.01); *C07K 2317/56* (2013.01); *C07K 2317/565* (2013.01); *C07K 2317/569* (2013.01); *C07K 2317/76* (2013.01)

(58) Field of Classification Search
CPC ....... A61K 39/395; C07K 16/22; A61P 19/08; A61P 19/10
See application file for complete search history.

(56) References Cited

U.S. PATENT DOCUMENTS

| | | |
|---|---|---|
| 5,219,996 A | 6/1993 | Bodmer et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,667,425 A | 9/1997 | Pineau et al. |
| 5,698,426 A | 12/1997 | Huse |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,821,047 A | 10/1998 | Garrard et al. |
| 5,969,108 A | 10/1999 | McCafferty et al. |
| 6,632,927 B2 | 10/2003 | Adair et al. |
| 9,631,011 B2 | 4/2017 | Kim et al. |
| 10,377,817 B2 | 8/2019 | Economides et al. |
| 10,947,304 B2 | 3/2021 | Dedi et al. |
| 11,524,997 B2 | 12/2022 | Davies et al. |
| 11,807,680 B2 | 11/2023 | Dedi et al. |
| 2007/0293425 A1 | 12/2007 | Muller et al. |
| 2009/0041757 A1 | 2/2009 | Zhen et al. |
| 2015/0158938 A1 | 6/2015 | Kim et al. |
| 2015/0183853 A1 | 7/2015 | Sharma et al. |
| 2016/0024195 A1 | 1/2016 | Economides et al. |
| 2019/0330323 A1 | 10/2019 | Dedi et al. |
| 2021/0163586 A1 | 6/2021 | Dedi et al. |
| 2021/0253688 A1 | 8/2021 | Davies et al. |
| 2024/0076365 A1 | 3/2024 | Dedi et al. |

FOREIGN PATENT DOCUMENTS

| | | |
|---|---|---|
| EP | 0 392 745 | 10/1990 |
| EP | 0 438 474 | 7/1991 |
| EP | 0 463 151 | 1/1992 |
| EP | 0 546 073 | 6/1993 |

(Continued)

OTHER PUBLICATIONS

Knappik et al., J. Mol. Biol., 2000, vol. 296(1):57-86.*
Rabia et al., Biochem. Eng. J., 2018, vol. 137:365-374.*
Phillips et al., Orthopaedic Proceedings, 2009, vol. 91-B(SUPP_I):113-113.*
Yin, M. et al. "Gremlin-1 is a key regulator of the invasive cell phenotype in mesothelioma" *Oncology*, 2017, pp. 98280-98297, vol. 8, No. 58.
Sebald, H.-J. et al. "Inhibition of endogenous antagonists with an engineered BMP-2 variant increases BMP-2 efficacy in rat femoral defect healing" *Acta Biomaterialia*, Oct. 10, 2012, pp. 3816-3820, vol. 8, No. 10.
Gazzerro, E. et al. "Skeletal Overexpression of Gremlin Impairs Bone Formation and Causes Osteopenia" *Endocrinology*, Feb. 1, 2005, pp. 655-665, vol. 146, No. 2.

(Continued)

*Primary Examiner* — Xiaozhen Xie
(74) *Attorney, Agent, or Firm* — SALIWANCHIK, LLOYD & EISENSCHENK

(57) ABSTRACT

The present invention relates to methods for the treatment of a bone fracture or bone defect. The invention discloses the effective use of an anti-gremlin-1 antibody to accelerate the healing and bridging of bone tissue in segmental gap defects; and demonstrates that inhibitors of gremlin-1 activity may provide improved therapies for treating or preventing fracture non-union.

4 Claims, 7 Drawing Sheets

Specification includes a Sequence Listing.

(56) References Cited

FOREIGN PATENT DOCUMENTS

| EP | 1 571 159 | 9/2005 |
|---|---|---|
| EP | 2 826 790 | 1/2015 |
| WO | WO 86/01533 | 3/1986 |
| WO | WO 89/00195 | 1/1989 |
| WO | WO 89/01476 | 2/1989 |
| WO | WO 90/02809 | 3/1990 |
| WO | WO 91/09967 | 7/1991 |
| WO | WO 91/10737 | 7/1991 |
| WO | WO 92/01047 | 1/1992 |
| WO | WO 92/02551 | 2/1992 |
| WO | WO 92/18619 | 10/1992 |
| WO | WO 92/22583 | 12/1992 |
| WO | WO 92/22853 | 12/1992 |
| WO | WO 93/06231 | 4/1993 |
| WO | WO 93/11236 | 6/1993 |
| WO | WO 95/15982 | 6/1995 |
| WO | WO 95/20401 | 8/1995 |
| WO | WO 98/25971 | 6/1998 |
| WO | WO 02/054940 | 7/2002 |
| WO | WO 03/031581 | 4/2003 |
| WO | WO 2004/051268 | 6/2004 |
| WO | WO 2004/106377 | 12/2004 |
| WO | WO 2005/003169 | 1/2005 |
| WO | WO 2005/003170 | 1/2005 |
| WO | WO 2005/003171 | 1/2005 |
| WO | WO 2005/113605 | 12/2005 |
| WO | WO 2005/117984 | 12/2005 |
| WO | WO 2007/124486 | 11/2007 |
| WO | WO 2008/038024 | 4/2008 |
| WO | WO 2009/040562 | 4/2009 |
| WO | WO 2013/137686 | 9/2013 |
| WO | WO 2014/159010 | 10/2014 |
| WO | WO 2018/115017 | 6/2018 |
| WO | WO 2019/243801 | 12/2019 |

OTHER PUBLICATIONS

Fajardo, M. et al. "Levels of Expression for BMP-7 and Several BMP Antagonists May Play an Integral Role in a Fracture Nonunion: A Pilot Study" *Clinical Orthopaedics and Related Research*, Jul. 14, 2009, pp. 3071-3078, vol. 467, No. 12.
Dean, D. B. et al. "Distinct functionalities of bone morphogenetic protein antagonists during fracture healing in mice" *Journal of Anatomy*, 2020, pp. 625-630, vol. 216, No. 5.
International Search Report and Written Opinion in International Application No. PCT/EP2019/053726, May 17, 2019, pp. 1-19.
Hu, K. et al. "Gremlin-1 suppression increases BMP-2-induced osteogenesis of human mesenchymal stem cells" *Molecular Medicine Reports*, 2017, pp. 2186-2194, vol. 15.
Adair, J. R. et al. "Therapeutic Antibodies" *Drug Design Reviews*, 2005, pp. 1-11.
Altschul, S.F. et al. "Basic Local Alignment Search Tool" *J Mol Biol.*, 1990, pp. 403-410, vol. 215.
Altschul, S.F. "A Protein Alignment Scoring System Sensitive at All Evolutionary Distances" *J Mol Evol.*, 1993, pp. 290-300, vol. 36.
Ames, R. S. et al. "Conversion of murine Fabs isolated from a combinatorial phage display library to full length immunoglobulins" *Journal of Immunological Methods*, 1995, pp. 177-186, vol. 184.
Angal, S. et al. "A Single Amino Acid Substitution Abolishes the Heterogeneity of Chimeric Mouse/Human (IgG4) Antibody" *Molecular Immunology*, 1993, pp. 105-108, vol. 30, No. 1.
Attar-Schneider, O. et al. "Multiple Myeloma and Bone Marrow Mesenchymal Stem Cells' Crosstalk: Effect on Translation Initiation" *Molecular Carcinogenesis*, 2016, pp. 1343-1354, vol. 55.
Azab, A. K. et al. "Hypoxia promotes dissemination of multiple myeloma through acquisition of epithelial to mesenchymal transition-like features" *Blood*, Jun. 14, 2012, pp. 5782-5794, vol. 119, No. 24.
Babcook, J. et al. "A novel strategy for generating monoclonal antibodies from single, isolated lymphocytes producing antibodies of defined specificities" *Proc. Natl. Acad. Sci. USA*, Jul. 1996, pp. 7843-7848, vol. 93, No. 15.

Badesch, D. B. et al. "Diagnosis and Assessment of Pulmonary Arterial Hypertension" *J Am Coll Cardiol.*, Jun. 30, 2009, pp. S55-S66, vol. 54, No. 1, Suppl. S.
Bostrom, M. P. G. et al. "The Clinical Use of Allografts, Demineralized Bone Matrices, Synthetic Bone Graft Substitutes and Osteoinductive Growth Factors: A Survey Study" *HSS Journal: The Musculoskeletal Journal of Hospital for Special Surgery*, 2005, pp. 9-18, vol. 1.
Brinkmann, U. et al. "Phage display of disulfide-stabilized Fv fragments" *Journal of Immunological Methods*, 1995, pp. 41-50, vol. 182.
Budd, D. C. et al. "Targeting TGFβ superfamily ligand accessory proteins as novel therapeutics for chronic lung disorders" *Pharmacology & Therapeutics*, 2012, pp. 279-291, vol. 135.
Burton, D. R. et al. "Human Antibodies from Combinatorial Libraries" *Advances in Immunology*, 1994, pp. 191-280, vol. 57.
Buza, J. A. et al. "Bone healing in 2016" *Clinical Cases in Mineral and Bone Metabolism*, 2016, pp. 101-105, vol. 13, No. 2.
Cahill, E. et al. "Gremlin Plays a Key Role in the Pathogenesis of Pulmonary Hypertension" *Circulation*, Feb. 21, 2012, pp. 920-930, vol. 125, No. 7.
Calon, A. et al. "Stromal gene expression defines poor-prognosis subtypes in colorectal cancer" *Nat Genet.*, Apr. 2015, pp. 320-329, vol. 47, No. 4, Online Methods, pp. 1-3.
Canalis, E. et al. "Gremlin1 is Required for Skeletal Development and Postnatal Skeletal Homeostasis" *J. Cell Physiol.*, 2012, pp. 269-277, vol. 227.
Chen, V. B. et al. "MolProbity: all-atom structure validation for macromolecular crystallography" *Acta Crystallographica Section D*, 2010, pp. 12-21, D66.
Chen, M.-H. et al. "Expression of gremlin 1 correlates with increased angiogenesis and progression-free survival in patients with pancreatic neuroendocrine tumors" *J Gastroenterol*, 2013, pp. 101-108, vol. 48.
Chen, J. et al. "BAFF is involved in macrophage-induced bortezomib resistance in myeloma" *Cell Death Dis*, 2017, pp. 1-12, vol. 8, No. 11, e3161.
Cheong, C. M. et al. "Tetraspanin 7 (TSPAN7) expression is upregulated in multiple myeloma patients and inhibits myeloma tumour development in vivo" *Exp Cell Res*, 2015, pp. 24-38, vol. 332.
Chesi, M. et al. "Drug response in a genetically engineered mouse model of multiple myeloma is predictive of clinical efficacy" *Blood*, Jul. 12, 2012, pp. 376-385, vol. 120, No. 2.
Cho, T.-J. et al. "Differential Temporal Expression of Members of the Transforming Growth Factor β Superfamily During Murine Fracture Healing" *Journal of Bone and Mineral Research*, Nov. 3, 2002, pp. 513-520, vol. 17, No. 3.
Ciuclan, L. et al. "Imatinib Attenuates Hypoxia-induced Pulmonary Arterial Hypertension Pathology via Reduction in 5-Hydroxytryptamine through Inhibition of Tryptophan Hydroxylase 1 Expression" *Am J Respir Crit Care Med.*, 2013, pp. 78-89, vol. 187, Issue 1.
Ciuclan, L, et al. "Treatment with Anti-Gremlin 1 Antibody Ameliorates Chronic Hypoxia/SU5416-Induced Pulmonary Arterial Hypertension in Mice" *Am J Pathol.*, Nov. 2013, pp. 1461-1473, vol. 183, No. 5.
Curran, S. P. et al. "Deletion of Gremlin1 increases cell proliferation and migration responses in mouse embryonic fibroblasts" *Cellular Signalling*, 2012, pp. 889-898, vol. 24, No. 4.
Dallas, S. L. et al. "Ibandronate Reduces Osteolytic Lesions but not Tumor Burden in a Murine Model of Myeloma Bone Disease" *Blood*, Mar. 1, 1999, pp. 1697-1706, vol. 93, No. 5.
Das, D. S. et al. "A novel hypoxia-selective epigenetic agent RRx-001 triggers apoptosis and overcomes drug resistance in multiple myeloma cells" *Leukemia*, 2016, pp. 2187-2197, vol. 30, No. 11.
Davis, H. et al. "Aberrant epithelial GREM1 expression initiates colonic tumorigenesis from cells outside the stem cell niche" *Nat Med.*, Jan. 2015, pp. 62-70, vol. 21, No. 1, Online Methods, pp. 1-3.
Devereux, J. et al. "A comprehensive set of sequence analysis programs for the VAX" *Nucleic Acids Research*, 1984, pp. 387-395, vol. 12, No. 1.

(56) References Cited

OTHER PUBLICATIONS

Diamond, P. et al. "Targeted Disruption of the CXCL12/CXCR4 Axis Inhibits Osteolysis in a Murine Model of Myeloma-Associated Bone Loss" *J Bone Miner Res*, 2009, pp. 1150-1161, vol. 24, No. 7.
Dubowchik, G. M. et al. "Receptor-mediated and enzyme-dependent targeting of cytotoxic anticancer drugs" *Pharmacology and Therapeutics*, 1999, pp. 67-123, vol. 83.
Einhorn, T. A. et al. "Fracture healing: mechanisms and interventions" *Nat. Rev. Rheumatol.*, Jan. 2015, pp. 45-54, vol. 11.
Emsley, P. et al. "Features and development of Coot" *Acta Crystallographica Section D: Biological Crystallography*, 2010, pp. 486-501, D66, No. 4.
Farber, H. W. et al. "Pulmonary Arterial Hypertension" *The New England Journal of Medicine*, 2004, pp. 1655-1665, vol. 351.
Ferguson, C. et al. "Does adult fracture repair recapitulate embryonic skeletal formation?" *Mechanisms of Development*, 1999, pp. 57-66, vol. 87.
Fowler, J. A. et al. "Bone Marrow Stromal Cells Create a Permissive Microenvironment for Myeloma Development: A New Stromal Role for Wnt Inhibitor Dkk1" *Cancer Research*, 2012, pp. 2183-2189, vol. 72, No. 9.
Gasteiger, E. et al. "Protein Identification and Analysis Tools on the ExPASy Server" *The Proteomics Protocols Handbook*, Humana Press, ed. J. M. Walker, 2005, pp. 571-607.
Gazzerro, E. et al. "Conditional Deletion of Gremlin Causes a Transient Increase in Bone Formation and Bone Mass" *J. Biol. Chem.*, Oct. 26, 2007, pp. 31549-31557, vol. 282, No. 43.
Ghobrial, I. M. "Myeloma as a model for the process of metastasis: implications for therapy" *Blood*, Jul. 5, 2012, pp. 20-30, vol. 120, No. 1.
Gilbane, A. J. et al. "Impaired Bone Morphogenetic Protein Receptor II Signaling in a Transforming Growth Factor-β-Dependent Mouse Model of Pulmonary Hypertension and in Systemic Sclerosis" *Am J Respir Crit Care Med.*, Mar. 15, 2015, pp. 665-677, vol. 191, Issue 6.
Goulet, J. A. et al. "Autogenous Iliac Crest Bone Graft. Complications and Functional Assessment" *Clinical Orthopaedics and Related Research*, Jun. 1997, pp. 76-81, No. 339.
Guan, Y. et al. "Gremlin1 promotes carcinogenesis of glioma in vitro" *Clin Exp Pharmacol Physiol*, 2017, pp. 244-256, vol. 44, No. 2.
Harris, R. J. "Processing of C-terminal lysine and arginine residues of proteins isolated from mammalian cell culture" *Journal of Chromatography A*, 1995, pp. 129-134, vol. 705.
Hellstrom, K. E. et al. "Antibodies for Drug Delivery" *Controlled Drug Delivery*, 2nd Ed., Robinson et al., eds., 1987, pp. 623-653.
Henikoff, S. et al. "Amino acid substitution matrices from protein blocks" *Proc. Natl. Acad. Sci. USA*, Nov. 1992, pp. 10915-10919, vol. 89.
Hewett, D. R. et al. "DNA Barcoding Reveals Habitual Clonal Dominance of Myeloma Plasma Cells in the Bone Marrow Microenvironment" *Neoplasia*, Dec. 2017, pp. 972-981, vol. 19, No. 4.
Hideshima, T. et al. "Understanding multiple myeloma pathogenesis in the bone marrow to identify new therapeutic targets" *Nature Reviews Cancer*, Aug. 2007, pp. 585-598, vol. 7, No. 8.
Hjertner, O. et al. "Bone morphogenetic protein-4 inhibits proliferation and induces apoptosis of multiple myeloma cells" *Blood*, Jan. 15, 2001, pp. 516-522, vol. 97, No. 2.
Hochleitner, E. O. et al. "Characterization of a discontinuous epitope of the human immunodeficiency virus (HIV) core protein p24 by epitope excision and differential chemical modification followed by mass spectrometric peptide mapping analysis" *Protein Science*, 2000, pp. 487-496, vol. 9.
Holien, T. et al. "Bone morphogenetic proteins induce apoptosis in multiple myeloma cells by Smad-dependent repression of MYC" *Leukemia*, 2012, pp. 1073-1080, vol. 26, No. 5.
Holliger, P. et al. "Engineered antibody fragments and the rise of single domains" *Nature Biotech.*, Sep. 2005, pp. 1126-1136, vol. 23, No. 9.
Howe, J. R. et al. "Mutations in the SMAD4/DPC4 Gene in Juvenile Polyposis" *Science*, May 15, 1998, pp. 1086-1088, vol. 280, No. 5366.
Howe. J. R. et al. "Germline mutations of the gene encoding bone morphogenetic protein receptor 1A in juvenile polyposis" *Nat Genet.*, Jun. 2001, pp. 184-187, vol. 28, No. 2.
Hsu, D. R. et al. "The Xenopus Dorsalizing Factor Gremlin Identifies a Novel Family of Secreted Proteins that Antagonize BMP Activities" *Molecular Cell*, Apr. 1998, pp. 673-683, vol. 1, No. 5.
International Search Report and Written Opinion in International Application No. PCT/GB2019/051699, Aug. 16, 2019, pp. 1-11.
Irshad, S. et al. "Bone morphogenetic protein and Notch signalling crosstalk in poor-prognosis, mesenchymal-subtype colorectal cancer" *J Pathol.*, 2017, pp. 178-192, vol. 242.
Isella, C. et al. "Stromal contribution to the colorectal cancer transcriptome" *Nat Genet.*, Apr. 2015, pp. 312-319, vol. 47, No. 4, Online Methods, pp. 1-4.
Jaeger, E. et al. "Hereditary mixed polyposis syndrome is caused by a 40-kb upstream duplication that leads to increased and ectopic expression of the BMP antagonist GREM1" *Nat Genet.*, Jun. 2012, pp. 699-703, vol. 44, No. 6, Online Methods, pp. 1-2.
Junghans, R. P. et al. "Anti-Tac-H, a Humanized Antibody to the Interleukin 2 Receptor with New Features for Immunotherapy in Malignant and Immune Disorders" *Cancer Res.*, Mar. 1, 1990, pp. 1495-1502, vol. 50.
Kabsch, W. "XDS" *Acta Crystallographica Section D, Biological Crystallography*, 2010, pp. 125-132, vol. D66.
Karagiannis, G. S. et al. "Enrichment map profiling of the cancer invasion front suggests regulation of colorectal cancer progression by the bone morphogenetic protein antagonist, gremlin-1" *Mol Oncol.*, 2013, pp. 826-839, vol. 7, No. 4.
Karagiannis, G. S. et al. "Bone morphogenetic protein antagonist gremlin-1 regulates colon cancer progression" *Biol Chem.*, 2015, pp. 163-183, vol. 396, No. 2.
Karlin, S. et al. "Applications and statistics for multiple high-scoring segments in molecular sequences" *Proc. Natl. Acad. Sci. USA*, Jun. 1993, pp. 5873-5877, vol. 90.
Kashmiri, S. V. S. et al. "SDR grafting—a new approach to antibody humanization" *Methods*, 2005, pp. 25-34, vol. 36.
Kettleborough, C. A. et al. "Isolation of tumor cell-specific single-chain Fv from immunized mice using phage-antibody libraries and the re-construction of whole antibodies from these antibody fragments" *Eur. J. Immunol.*, 1994, pp. 952-958, vol. 24.
Kim, M. et al. "Gremlin-1 Induces BMP-Independent Tumor Cell Proliferation, Migration, and Invasion" *PloS One*, Apr. 2012, pp. 1-8, vol. 7, Issue 4, e35100.
Kim, H. S. et al. "GREM1 is expressed in the cancer-associated myofibroblasts of basal cell carcinomas" *PloS One*, 2017, pp. 1-13, vol. 12, No. 3, e0174565.
Kohler, G. et al. "Continuous cultures of fused cells secreting antibody of predefined specificity" *Nature*, Aug. 7, 1975, pp. 495-497, vol. 256.
Koketsu, K. et al. "Gremlin, a Bone Morphogenetic Protein Antagonist, Is a Crucial Angiogenic Factor in Pituitary Adenoma" *Int J Endocrinol.*, 2015, pp. 1-7, Article ID 834137.
Kozbor, D. et al. "The production of monoclonal antibodies from human lymphocytes" *Immunology Today*, 1983, pp. 72-79, vol. 4, No. 3.
Krinner, E.-M. et al. "A human monoclonal IgG1 potently neutralizing the pro-inflammatory cytokine GM-CSF" *Mol. Immunol.*, Feb. 2007, pp. 916-925, vol. 44, No. 5.
Kyle, R. A. et al. "Multiple Myeloma" *N Engl J Med*, 2004, pp. 1860-1873, vol. 351, No. 18.
Laurila, R. et al. "The expression patterns of gremlin 1 and noggin in normal adult and tumor tissues" *Int J Clin Exp Pathol.*, 2013, pp. 1400-1408, vol. 6, No. 7.
Lavoz, C. et al. "Gremlin regulates renal inflammation via the vascular endothelial growth factor receptor 2 pathway" *J Pathol.*, 2015, pp. 407-420, vol. 236.
Lawson, M. A. et al. "Osteoclasts control reactivation of dormant myeloma cells by remodelling the endosteal niche" *Nat Commun.*, 2015, pp. 1-15, vol. 6, 8983.

(56) References Cited

OTHER PUBLICATIONS

Lewis, A. et al. "A Polymorphic Enhancer Near GREM1 Influences Bowel Cancer Risk through Differential CDX2 and TCF7L2 Binding" *Cell Rep.*, Aug. 21, 2014, pp. 983-990, vol. 8, No. 4.

McCoy, A. J. et al. "Phaser crystallographic software" *J Appl Cryst.*, 2007, pp. 658-674, vol. 40.

Mitola, S. et al. "Gremlin is a novel agonist of the major proangiogenic receptor VEGFR2" *Blood*, Nov. 4, 2010, pp. 3677-3680, vol. 116, No. 18.

Mulvihill, M. S. et al. "Gremlin is Overexpressed in Lung Adenocarcinoma and Increases Cell Growth and Proliferation in Normal Lung Cells" *PloS One*, 2012, pp. 1-8, vol. 7, No. 8, e42264.

Murshudov, G. N. et al. "REFMAC5 for the refinement of macromolecular crystal structures" *Acta Crystallographica Section D: Biological Crystallography*, 2011, pp. 355-367, vol. D67.

Namkoong, H. et al. "The bone morphogenetic protein antagonist gremlin 1 is overexpressed in human cancers and interacts with YWHAH protein" *BMC Cancer*, 2006, pp. 1-13, vol. 6, No. 74.

Neufert, C. et al. "An inducible mouse model of colon carcinogenesis for the analysis of sporadic and inflammation-driven tumor progression" *Nat Protoc.*, 2007, pp. 1998-2004, vol. 2, No. 8.

Nolan, K. et al. "Structure of Protein Related to Dan and Cerberus: Insights into the Mechanism of Bone Morphogenetic Protein Antagonism" *Structure*, Aug. 6, 2013, pp. 1417-1429, vol. 21.

Nolan, K. et al. "Structure of Neuroblastoma Suppressor of Tumorigenicity 1 (NBL1)" *J. Biol. Chem.*, Feb. 20, 2015, pp. 4759-4771, vol. 290, No. 8.

Noll, J. E. et al. "Myeloma plasma cells alter the bone marrow microenvironment by stimulating the proliferation of mesenchymal stromal cells" *Haematologica*, 2014, pp. 163-171, vol. 99, No. 1.

Noll, J. E. et al. "SAMSN1 Is a Tumor Suppressor Gene in Multiple Myeloma" *Neoplasia*, Jul. 2014, pp. 572-585, vol. 16, No. 7.

Noll, J. E. et al. "PTTG1 expression is associated with hyperproliferative disease and poor prognosis in multiple myeloma" *J Hematol Oncol.*, 2015, pp. 1-16, vol. 8, No. 106.

Persic, L. et al. "An integrated vector system for the eukaryotic expression of antibodies or their fragments after selection from phage display libraries" *Gene*, 1997, pp. 9-18, vol. 187.

Plaks, V. et al. "The Cancer Stem Cell Niche: How Essential Is The Niche in Regulating Sternness of Tumor Cells?" *Cell Stem Cell*, Mar. 5, 2015, pp. 225-238, vol. 16, No. 3.

Ponomarev, V. et al. "A novel triple-modality reporter gene for whole-body fluorescent, bioluminescent, and nuclear noninvasive imaging" *Eur J Nucl Med Mol Imaging*, 2004, pp. 740-751, vol. 31, No. 5.

Reineke, U. "Antibody Epitope Mapping Using Arrays of Synthetic Peptides" *Methods Mol Biol*, 2004, pp. 443-463, vol. 248.

Retter, I. et al. "VBASE2, an integrative V gene database" *Nucl. Acids Res.*, 2005, pp. D671-D674, vol. 33.

Riechmann, L. et al. "Reshaping human antibodies for therapy" *Nature*, Mar. 24, 1998, pp. 323-327, vol. 332.

Sato, T. et al. "Single Lgr5 stem cells build crypt-villus structures in vitro without a mesenchymal niche" *Nature*, May 14, 2009, pp. 262-265, vol. 459, No. 7244, Methods, p. 1.

Sato, K. et al. "Establishment of Reproducible, Critical-Sized, Femoral Segmental Bone Defects in Rats" *Tissue Eng Part C.*, 2014, pp. 1037-1041, vol. 20, No. 12.

Schmid, G. J. et al. "Fibroblast Growth Factor Expression During Skeletal Fracture Healing in Mice" *Developmental Dynamics*, 2009, pp. 766-774, vol. 238.

Scoville, D. H. et al. "Current View: Intestinal Stem Cells and Signaling" *Gastroenterology*, 2008, pp. 849-864, vol. 134, No. 3.

Search Report for GB1802486.9, Oct. 17, 2018, pp. 1-5.

Sethi, A. et al. "Gremlin utilizes canonical and non-canonical TGFβ signaling to induce lysyl oxidase (LOX) genes in human trabecular meshwork cells" *Exp Eye Res.*, 2013, pp. 117-127, vol. 113.

Shoshkes-Carmel, M. et al. "Subepithelial telocytes are an important source of Wnts that supports intestinal crypts" *Nature*, May 10, 2018, pp. 242-246, vol. 557, Supplemental pp. 1-9.

Simonneau, G. et al. "Updated Clinical Classification of Pulmonary Hypertension" *J Am Coll Cardiol.*, Jun. 30, 2009, pp. S43-S54, vol. 54, No. 1, Suppl S.

Sneddon, J. B. et al. "Bone morphogenetic protein antagonist gremlin 1 is widely expressed by cancer-associated stromal cells and can promote tumor cell proliferation" *Proc Natl Acad Sci USA*, Oct. 3, 2006, pp. 14842-14847, vol. 103, No. 40.

Tamminen, J.A. et al. "Gremlin-1 associates with fibrillin microfibrils in vivo and regulates mesothelioma cell survival through transcription factor slug" *Oncogenesis*, 2013, pp. 1-13, vol. 2, e66.

Thomas, M. et al. "Activin-like kinase 5 (ALK5) Mediates Abnormal Proliferation of Vascular Smooth Muscle Cells from Patients with Familial Pulmonary Arterial Hypertension and Is Involved in the Progression of Experimental Pulmonary Arterial Hypertension Induced by Monocrotaline" *Am J Pathol.*, Feb. 2009, pp. 380-389, vol. 174, No. 2.

Thorpe, P. E. et al. "The Preparation and Cytotoxic Properties of Antibody-Toxin Conjugates" *Immunol. Rev.*, 1982, pp. 119-158, vol. 62.

Tomlinson, I. P. M. et al. "Multiple Common Susceptibility Variants near BMP Pathway Loci GREM1, BMP4, and BMP2 Explain Part of the Missing Heritability of Colorectal Cancer" *PLoS Genet.*, Jun. 2011, pp. 1-11, vol. 7, No. 6, e1002105.

Topol, L. Z. et al. "Identification of drm, a Novel Gene Whose Expression Is Suppressed in Transformed Cells and Which Can Inhibit Growth of Normal but Not Transformed Cells in Culture" *Mol Cell Biol*, Aug. 1997, pp. 4801-4810, vol. 17, No. 8.

United Kingdom Search Report Application No. GB1519083.8, Jul. 29, 2016, pp. 1-5.

Vande Broek, I. et al. "Extravasation and homing mechanisms in multiple myeloma" *Clin Exp Metastasis*, 2008, pp. 325-334, vol. 25, No. 4.

Vaughan, T. J. et al. "Human antibodies by design" *Nature Biotechnology*, Jun. 1998, pp. 535-539, vol. 16.

Verheyden, J. M. et al. "An Fgf/Gremlin inhibitory feedback loop triggers termination of limb bud outgrowth" *Nature*, Jul. 31, 2008, pp. 1-12, vol. 454, No. 7204.

Verma, R. et al. "Antibody engineering: Comparison of bacterial, yeast, insect and mammalian expression systems" *Journal of Immunological Methods*, 1998, pp. 165-181, vol. 216.

Wang, D.-J. et al. "The bone morphogenetic protein antagonist Gremlin is overexpressed in human malignant mesothelioma" *Oncology Reports*, 2012, pp. 58-64, vol. 27, No. 1.

Worthley, D. L. et al. "Gremlin 1 Identifies a Skeletal Stem Cell with Bone, Cartilage, and Reticular Stromal Potential" *Cell*, Jan. 15, 2015, pp. 269-284, vol. 160, Nos. 1-2.

Written Opinion in International Application No. PCT/EP2017/083650, Jan. 4, 2019, pp. 1-8.

Yin, Y. et al. "Overexpression of Gremlin promotes non-small cell lung cancer progression" *Tumour Biol*, 2016, pp. 2597-2602, vol. 37.

Yu, Y. Y. et al. "Immunolocalization of BMPs, BMP antagonists, receptors, and effectors during fracture repair" *Bone*, 2010, pp. 841-851, vol. 46.

United Kingdom Search Report Application No. GB1809946.5, Jan. 24, 2019, pp. 1-4.

Walsh, D.W. et al. "Extracellular BMP-antagonist regulation in development and disease: tied up in knots" *Trends in Cell Biology*, Feb. 24, 2010, pp. 244-256, vol. 20, No. 5.

Torre, L.A. et al. "Global Cancer in Women: Burden and Trends" *Cancer Epidemiol Biomarkers Prev*, Feb. 21, 2017, pp. 444-457, vol. 26, No. 4.

"Breast Cancer Facts & Figures 2015-2016" *American Cancer Society*, 2015, 2 cover pages and pp. 1-40.

Mittal, S. et al. "The breast tumour microenvironment—role in cancer development, progression and response to therapy" *Expert Review of Molecular Diagnostics*, 2018, pp. 1-34, vol. 18, No. 3.

Merino, R. et al. "The BMP antagonist Gremlin regulates outgrowth, chondrogenesis and programmed cell death in the developing limb" *Development*, 1999, pp. 5515-5522, vol. 126.

Schuetz, C. S. et al. "Progression-Specific Genes Identified by Expression Profiling of Matched Ductal Carcinomas In situ and Invasive Breast Tumors, Combining Laser Capture Microdissection

(56) References Cited

OTHER PUBLICATIONS and Oligonucleotide Microarray Analysis" *Cancer Research*, May 15, 2006, pp. 5278-5286, vol. 66, No. 10.
Kuchimaru, T. et al. "A reliable murine model of bone metastasis by injecting cancer cells through caudal arteries" *Nature Communications*, 2018, pp. 1-7, vol. 9, No. 2981.
Kager, L. et al. "Novel insights and therapeutic interventions for pediatric osteosarcoma" *Future Oncol.*, Sep. 21, 2016, pp. 357-368, vol. 13, No. 4.
Kresse, S. H. et al. "Integrative Analysis Reveals Relationships of Genetic and Epigenetic Alterations in Osteosarcoma" *PLoS One*, Nov. 7, 2012, pp. 1-20, vol. 7, Issue 11, e48262.
Groeneveld, E. H. J. et al. "Bone morphogenetic proteins in human bone regeneration" *European Journal of Endocrinology*, 2000, pp. 9-21, vol. 142.
Zysk, A. et al. "Zoledronate Enhances the Cytotoxicity of Gamma Delta T Cell Immunotherapy in an Orthotopic Mouse Model of Osteolytic Osteosarcoma" *J Cancer Sci Ther*, 2018, pp. 262-266, vol. 10, No. 9.
Tian, H. et al. "Bone morphogenetic protein-2 and tumor growth: Diverse effects and possibilities for therapy" *Cytokine & Growth Factor Reviews*, 2017, pp. 73-91, vol. 34.
Tian, H. et al. "Bone Morphogenetic Protein-2 Promotes Osteosarcoma Growth by Promoting Epithelial-Mesenchymal Transition (EMT) Through the Wnt/β-Catenin Signaling Pathway" *Journal of Orthopaedic Research*, Jul. 2019, pp. 1638-1648.
Nguyen, A. et al. "Roles of bone morphogenetic protein signaling in osteosarcoma" *International Orthopaedics (SICOT)*, 2014, pp. 2313-2322, vol. 38.
Rycaj, K. et al. "Cellular determinants and microenvironmental regulation of prostate cancer metastasis" *Semin Cancer Biol.*, Jun. 2017, pp. 1-35, vol. 44.
Grillo, E. et al. "Monomeric gremlin is a novel vascular endothelial growth factor receptor-2 antagonist" *Oncotarget*, May 11, 2016, pp. 35353-35368, vol. 7, No. 23.
Gandaglia, G. et al. "Impact of the Site of Metastases on Survival in Patients with Metastatic Prostate Cancer" *European Urology*, 2015, pp. 325-334, vol. 68.
Armstrong, A. J. et al. "A Contemporary Prognostic Nomogram for Men with Hormone-Refractory Metastatic Prostate Cancer: A TAX327 Study Analysis" *Clin Cancer Res*, Nov. 1, 2007, pp. 6396-6403, vol. 13, No. 21.
Van Cutsem, E. et al. "Metastatic colorectal cancer: ESMO Clinical Practice Guidelines for diagnosis, treatment and follow-up" *Annals of Oncology*, Sep. 2014, pp. ii1-ii9, vol. 25 (Supplement 3).
Muñoz, J. et al. "The Lgr5 intestinal stem cell signature: robust expression of proposed quiescent '+4' cell markers" *The EMBO Journal*, 2012, pp. 3079-3091, vol. 31, No. 14.
Moser, A. R. et al. "The Min (Multiple Intestinal Neoplasia) Mutation: Its Effect on Gut Epithelial Cell Differentiation and Interaction with a Modifier System" *The Journal of Cell Biology*, Mar. 1992, pp. 1517-1526, vol. 116, No. 6.
Shibata, H. et al. "Rapid Colorectal Adenoma Formation Initiated by Conditional Targeting of the Apc Gene" *Science*, Oct. 3, 1997, pp. 120-123, vol. 278.
El Marjou, F. et al. "Tissue-Specific and Inducible Cre-Mediated Recombination in the Gut Epithelium" *genesis*, 2004, pp. 186-193, vol. 39.
Rudling, R. et al. "A simple device to rapidly prepare whole mounts of murine intestine" *Cell Prolif.*, 2006, pp. 415-420, vol. 39.
Sato, T. et al. "Long-Term Expansion of Epithelial Organoids From Human Colon, Adenoma, Adenocarcinoma, and Barrett's Epithelium" *Gastroenterology*, Nov. 2011, pp. 1762-1772, vol. 141, No. 5.

Rudikoff, S. et al. "Single amino acid substitution altering antigen-binding specificity" *Proceedings of the National Academy of Sciences of the United States of America*, Mar. 1982, pp. 1979-1983, vol. 79, No. 6.
Janeway, Jr., C. A. et al. Immunology: the immune system in health and disease, 3rd ed., 1997, Garland Publications, Inc., Chapter 3, "Structure of the Antibody Molecule and Immunoglobulin Genes" pp. 3:1-3: 11.
Lederman, S. et al. "A Single Amino Acid Substitution in a Common African Allele of the CD4 Molecule Ablates Binding of the Monoclonal Antibody, OKT4" *Molecular Immunology*, 1991, pp. 1171-1181, vol. 28, No. 11.
Li, J. et al. "Temporal associations between interleukin 22 and the extracellular domains of IL-22R and IL-IOR2" *International Immunology*, 2004, pp. 693-711, vol. 4.
Panka, D. J. et al. "Variable region framework differences result in decreased or increased affinity of variant anti-digoxin antibodies" *Proceedings of the National Academy of Sciences of the United States of America*, May 1, 1988, pp. 3080-3084, vol. 85, No. 9.
Amit, A. G. et al. "Three-Dimensional Structure of an Antigen-Antibody Complex at 2.8 Å Resolution" *Science*, Aug. 15, 1986, pp. 747-753, vol. 233, No. 4765.
Harlow, E. et al. "Antibodies, A Laboratory Manual" *Cold Spring Harbor Laboratory*, 1988, Chapter 5, pp. 1-2.
O'Reilly, S. et al. "Interleukin-6 (IL-6) Trans Signaling Drives a STAT3-dependent Pathway That Leads to Hyperactive Transforming Growth Factor-β (TGF-β) Signaling Promoting SMAD3 Activation and Fibrosis via Gremlin Protein" *The Journal of Biological Chemistry*, Apr. 4, 2014, pp. 9952-9960, vol. 289, No. 14.
Sato, M. et al. "Clinical significance of Gremlin 1 in cervical cancer and its effects on cancer stem cell maintenance" *Oncology Reports*, 2016, pp. 391-397, vol. 35.
Uchiyama, H. et al. "Adhesion of Human Myeloma-Derived Cell Lines to Bone Marrow Stromal Cells Stimulates Interleukin-6 Secretion" *Blood*, Dec. 15, 1993, pp. 3712-3720, vol. 82, No. 12.
Van Vlodrop, I. J. H. et al. "Prognostic Significance of Gremlin1 (GREM1) Promoter CpG Island Hypermethylation in Clear Cell Renal Cell Carcinoma" *The American Journal of Pathology*, Feb. 2010, pp. 575-584, vol. 176, No. 2.
Yu, Y. et al. "Overexpression of Gremlin 1 by sonic hedgehog signaling promotes pancreatic cancer progression" *International Journal of Oncology*, 2018, pp. 2445-2457, vol. 53.
Clark, K. C. et al. "Targeted Disruption of Bone Marrow Stromal Cell-Derived Gremlin1 Limits Multiple Myeloma Disease Progression In Vivo" *Cancers*, Aug. 3, 2020, pp. 1-20, vol. 12, No. 2149.
Knappik, A. et al. "Fully Synthetic Human Combinatorial Antibody Libraries (HuCAL) Based on Modular Consensus Frameworks and CDRs Randomized with Trinucleotides" *J. Mol. Biol.*, 2000, pp. 57-86, vol. 296, No. 1.
Park, S.-A. et al. "Gremlin-1 augments the oestrogen-related receptor α signalling through EGFR activation: implications for the progression of breast cancer" *British Journal of Cancer*, published online Jun. 23, 2020, pp. 988-999, vol. 123, No. 6.
Cao, A. et al. "Beta-thalassemia" *Genetics In Medicine*, Feb. 2010, pp. 61-76, vol. 12, No. 2.
Dabrowski, M. et al. "Diffuse Idiopathic Skeletal Hyperostosis of Cervical Spine with Dysphagia—Molecular and Clinical Aspects" *International Journal of Molecular Sciences*, Apr. 20, 2021, pp. 1-12, vol. 22, No. 4255.
Honma, R. et al. "Clinicopathological and Prognostic Significance of Epithelial Gremlin1 Expression in Gastric Cancer" *Anticancer Research*, 2018, pp. 1419-1425, vol. 38.

\* cited by examiner

GREMLIN-1 INHIBITOR FOR THE TREATMENT OF A BONE FRACTURE OR BONE DEFECT

CROSS-REFERENCE TO RELATED APPLICATIONS

This application is a continuation of U.S. application Ser. No. 16/970,391, filed Aug. 17, 2020, now U.S. Pat. No. 11,524,997, which is the U.S. national stage application of International Patent Application No. PCT/EP2019/053726, filed Feb. 14, 2019.

The Sequence Listing for this application is labeled "Seq-List.xml" which was created on Dec. 3, 2022 and is 54,273 bytes. The entire content of the sequence listing is incorporated herein by reference in its entirety.

The present invention relates to methods for the treatment of a bone fracture or bone defect. The invention discloses the effective use of an anti-gremlin-1 antibody to accelerate the healing and bridging of bone tissue in segmental gap defects; and demonstrates that inhibitors of gremlin-1 activity may provide improved therapies for treating or preventing fracture non-union.

BACKGROUND

A bone fracture is a break or crack in bone tissue and may be the result of a traumatic injury, such as a fall or impact, but can also occur as a result of diseases that affect bone integrity.

Non-stabilised bone fractures heal through the process of endochondral ossification, which is initiated through the formation of a blood clot or haematoma. This is coupled with an inflammatory response that modulates immune cells and surrounding skeletal stem cell populations. The haematoma is subsequently replaced with a mineralised cartilaginous callus through the action of various growth factors including transforming growth factor beta (TGFP) (Cho et al; 2002), fibroblastic growth factors (FGFs) (Schmid et al; 2009), and bone morphogenic proteins (BMPs) (Yu et al; 2010). Through the actions of osteoclasts and osteoblasts, the mineralised callus is replaced by woven bone. The final remodelling stage involves the replacement of woven bone with lamellar bone. The completion of this process can take many years depending on the age and disease status of the patient.

Bone fractures are generally treated clinically through stabilisation, via the use of a support such as a splint, cast, or brace. In extreme cases involving complex fractures surgical intervention may be required and involves the use of internal and external fixators that are attached directly to the bone. Even with these measures, in approximately 10% of patients the tissue repair process is deficient (Einhorn et al; 2014) resulting in delayed bone union (failure to reach union 6 months post-fracture) or non-union. A non-union is defined as incomplete healing within 9 months, combined with a lack of radiological characteristics associated with fracture healing being observed over three consecutive months (Buza et al; 2016). Current surgical techniques for repairing non-union fractures and critical bone defects are often limited in terms of quantity and quality of the materials available. Commonly used treatments involve the autologous or allogenic graft, however these carry the additional risk of donor site morbidity (Goulet et al; 1997) and infection (Bostrom et al; 2005), respectively.

A bone defect is a loss of bone, due to trauma or disease. There is currently a great unmet medical need for improved treatment of bone fractures and bone defects. Accordingly, it is an object of the present invention to provide new methods for the treatment of a bone fracture or bone defect.

The present invention provides inhibitors of gremlin-1 activity for use in the treatment of a bone fracture or bone defect. The invention discloses the effective use of an anti-gremlin-1 antibody to accelerate the healing and bridging of bone tissue in segmental gap defects; and demonstrates that inhibitors of gremlin-1 activity may provide improved therapies for treating or preventing fracture non-union.

DESCRIPTION OF THE INVENTION

Unless defined otherwise, all scientific and technical terms used herein have the same meaning as commonly understood by one of skill in the art. All publications referred to herein are incorporated by reference.

It will be appreciated that any of the embodiments described herein may be combined.

The present invention provides an inhibitor of gremlin-1 activity for use in the treatment of a bone fracture or bone defect. The invention also provides the use of an inhibitor of gremlin-1 activity for the manufacture of a medicament for the treatment of a bone fracture or bone defect. The invention further provides a method for the treatment of a bone fracture or bone defect comprising administering a therapeutically effective amount of an inhibitor of gremlin-1 activity.

Gremlin-1 (also known as Drm and CKTSF1B1) is a 184 amino acid glycoprotein which forms part of the DAN family of cysteine-knot secreted proteins (along with Cerberus and Dan amongst others). Gremlin binds and inhibits the ability of BMP-2, 4, and 7 to signal along with a documented pro-angiogenic role possibly through agonism of VEGFR2. The main role of Gremlin-1 is during development, in which it is vital during kidney formation and during limb bud formation.

Bone morphogenetic protein (BMP) signalling is known to control endochondral bone formation, with Gremlin 1 (GREM1) being one of the natural antagonists of this pathway through its binding to BMP2, BMP4 and BMP7 (Hsu et al; 1998). GREM1 conditional deletion in osteoblasts results in sensitisation of BMP signalling/activity and enhanced bone formation in vivo (Gazzerro et al; 2007), whilst conditional overexpression in the same cell type causes osteopenia and spontaneous fractures (Gazzerro et al; 2005). Furthermore, although the global knockout is embryonic lethal in a BL6 background, 49% of pups survived longer than 24 hrs post birth in the C57BL/6/FVB mixed genetic background, and whilst developmental skeletal defects were abundantly present, elevated bone formation rates could be observed (Canalis et al; 2012). Despite this developmental function of GREM1 there is no data to suggest that inhibition of this protein alone will enhance postnatal bone fracture repair. Indeed, although endochondral bone formation is the main mechanism of skeletogenesis at embryonic stages, the mechanisms that regulate cell recruitment are distinct processes when compared to postnatal fracture repair (Ferguson et al; 1999). The role of inflammation has been indicated as a key factor in adult bone repair, thus developmental factors controlling skeletogenesis processes cannot simply be extrapolated to postnatal repair mechanisms.

The term Gremlin-1 as used in the present invention typically has the sequence as set out in the UniProt entry O60565 (SEQ ID NO: 1). The term Gremlin-1 may also refer to a Gremlin-1 polypeptide which:

(a) comprises or consists of the amino acid sequence of SEQ ID NO: 1 with or without the N-terminal signal peptide, i.e. may comprise or consist of the mature peptide sequence as shown in SEQ ID NO: 21; or (b) is a derivative having one or more amino acid substitutions, modifications, deletions or insertions relative to the amino acid sequence of SEQ ID NO: 1 with or without the N-terminal signal peptide (as shown in SEQ ID NO: 21), which retains the activity of Gremlin-1, such as the amino acid sequence of SEQ ID NO: 20;

(c) a variant thereof, such variants typically retain at least about 60%, 70%, 80%, 90%, 91%, 92%, 93%, 94% or 95% identity to SEQ ID NO: 1 (or SEQ ID NO: 20 or 21) (or even about 96%, 97%, 98% or 99% identity). In other words, such variants may retain about 60%—about 99% identity to SEQ ID NO: 1, suitably about 80%—about 99% identity to SEQ ID NO: 1, more suitably about 90%—about 99% identity to SEQ ID NO: 1 and most suitably about 95%—about 99% identity to SEQ ID NO: 1. Variants are described further below.

As discussed further below, residue numbers are typically quoted based on the sequence of SEQ ID NO: 1. However, residue numbering could readily be extrapolated by the skilled person to a derivative or variant sequence as discussed above. Where residue numbers are quoted, the invention also encompasses these residues on a variant or derivative sequence.

The present inventors have crystallised human Gremlin-1 alone, and in complex with an antibody termed Ab 7326 (Fab fragments). Crystallisation of Gremlin-1 has allowed putative residues in the BMP binding site to be determined. Furthermore, crystallisation with Ab 7326, which is an allosteric inhibitory antibody, has allowed residues in the antibody epitope to be determined. (WO 2018/115017 A2). Antibodies binding this epitope have potential as therapeutic agents in the treatment of a bone fracture or bone defect.

Inhibitors of Gremlin-1 Activity

An inhibitor of gremlin-1 activity according to the present invention is an agent that reduces or blocks the activity of gremlin-1. Inhibitors according to the present invention may partially or completely inhibit gremlin-1 activity. Inhibitors of use in the present invention include without limitation, inhibitors that are capable of binding to gremlin-1 or to a nucleic acid molecule encoding gremlin-1, or are capable of inhibiting the expression of gremlin-1. Such inhibitors may be, without limitation, proteins, polypeptides, peptides, peptidomimetics, nucleic acids (e.g. DNA, RNA, antisense RNA and siRNA), carbohydrates, lipids, and small molecules.

In one embodiment, the inhibitor of gremlin-1 activity is an anti-gremlin-1 antibody or a functionally active fragment, variant or derivative thereof.

The term "antibody" as referred to herein includes whole antibodies and any antigen binding fragment (i.e., "antigen-binding portion") or single chains thereof. An antibody or immunoglobulin typically refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as HCVR or $V_H$) and a heavy chain constant region. Each light chain is comprised of a light chain variable region (abbreviated herein as LCVR or $V_L$) and a light chain constant region. The variable regions of the heavy and light chains contain a binding domain that interacts with an antigen. The $V_H$ and $V_L$ regions can be further subdivided into regions of hypervariability, termed complementarity determining regions (CDR), interspersed with regions that are more conserved, termed framework regions (FR).

The constant regions of the antibodies may mediate the binding of the immunoglobulin to host tissues or factors, including various cells of the immune system (e.g., effector cells) and the first component (Clq) of the classical complement system.

An antibody for use in the present invention may be a monoclonal antibody or a polyclonal antibody, and will typically be a monoclonal antibody. An antibody for use in the invention may be a chimeric antibody, a CDR-grafted antibody, a nanobody, a human or humanised antibody or an antigen-binding portion of any thereof.

Polyclonal antibodies may be produced by routine methods, such as immunisation of a suitable animal with the antigen of interest. Blood may be subsequently removed from the animal and the immunoglobulin fraction purified.

Antibodies against Gremlin-1 may be obtained, where immunisation of an animal is necessary, by administering the polypeptides to an animal, e.g. a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, goats, cows, camels, llamas or pigs may be immunised. However, rabbits, mice, and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-78481; WO 92/02551; WO 2004/051268 and WO 2004/106377.

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Fully human antibodies are those antibodies in which the variable regions and the constant regions (where present) of both the heavy and the light chains are all of human origin, or substantially identical to sequences of human origin, but not necessarily from the same antibody. Examples of fully human antibodies may include antibodies produced, for example by the phage display methods described above and antibodies produced by mice in which the murine immunoglobulin variable and optionally the constant region genes have been replaced by their human counterparts e.g. as described in general terms in EP 0546073, U.S. Pat. Nos. 5,545,806, 5,569,825, 5,625,126, 5,633,425, 5,661,016, 5,770,429, EP 0438474 and EP 0463151.

Alternatively, an antibody according to the invention may be produced by a method comprising immunising a non-human mammal with a Gremlin-1 immunogen; obtaining an antibody preparation from said mammal; deriving therefrom monoclonal antibodies that recognise Gremlin-1.

The antibody molecules for use in the present invention may comprise a complete antibody molecule having full length heavy and light chains or a fragment or antigen-binding portion thereof. The term "antigen-binding portion" of an antibody refers to one or more fragments of an antibody that retain the ability to selectively bind to an antigen. It has been shown that the antigen-binding function of an antibody can be performed by fragments of a full-length antibody. The antibodies and fragments and antigen binding portions thereof may be, but are not limited to Fab, modified Fab, Fab', modified Fab', F(ab')$_2$, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO 2005/003169, WO 2005/003170 and WO 2005/003171 and Fab-dAb fragments described in International patent application WO 2009/040562. Multi-valent antibodies may comprise multiple specificities or may be mono-specific (see for example WO 92/22853 and WO 2005/113605). These antibody fragments may be obtained using conventional techniques known to those of skill in the art, and the fragments may be screened for utility in the same manner as intact antibodies.

In one example, the functionally active antibody fragment for use in the present invention is a Fab, Fab', F(ab')2, Fv or scFv.

The constant region domains of the antibody molecule for use in the present invention, if present, may be selected having regard to the effector functions which may be required. For example, the constant region domains may be human IgA, IgD, IgE, IgG or IgM domains. In particular, human IgG constant region domains may be used, especially of the IgG1 and IgG3 isotypes when antibody effector functions are required. Alternatively, IgG2 and IgG4 isotypes may be used when antibody effector functions are not required. In one example, the isotype is IgG4P, as described by Angal S. et al, Mol Immunol, Vol 30(1), p 105-108, 1993.

An antibody for use in the invention may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

An antibody for use in the invention may be a human antibody or a humanised antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. Human antibodies for use in the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma that includes a B cell obtained from a transgenic nonhuman animal, e.g., a transgenic mouse, having a genome comprising a human heavy chain transgene and a light chain transgene fused to an immortalized cell.

Human antibodies may be prepared by in vitro immunisation of human lymphocytes followed by transformation of the lymphocytes with Epstein-Barr virus.

The term "derivative" refers to any modified form of the antibody, for example a conjugate of the antibody and another agent or effector molecule.

An effector molecule may comprise a single effector molecule or two or more such molecules so linked as to form a single moiety that can be attached to the antibodies for use in the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 2003/031581. Alternatively, where the effector molecule is a protein or polypeptide the linkage may be achieved using recombinant DNA procedures, for example as described in WO 86/01533 and EP 0392745.

The effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO 2005/117984.

The term "humanised antibody" is intended to refer to CDR-grafted antibody molecules in which CDR sequences derived from the germline of another mammalian species, such as a mouse, have been grafted onto human framework sequences. Additional framework region modifications may be made within the human framework sequences.

As used herein, the term 'CDR-grafted antibody molecule' refers to an antibody molecule wherein the heavy and/or light chain contains one or more CDRs (including, if desired, one or more modified CDRs) from a donor antibody (e.g. a murine or rat monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the CDR-grafted antibody for use in the present invention has a variable domain comprising human acceptor framework regions as well as one or more of the CDRs or specificity determining residues described above. Thus, provided in one embodiment is a neutralising CDR-grafted antibody wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available for example at: Worldwide Website: vbase2.org/(see Retter et al, Nucl. Acids Res. (2005) 33 (supplement 1), D671-D674).

In a CDR-grafted antibody for use in the present invention, the acceptor heavy and light chains do not necessarily need to be derived from the same antibody and may, if desired, comprise composite chains having framework regions derived from different chains.

Also, in a CDR-grafted antibody for use in the present invention, the framework regions need not have exactly the same sequence as those of the acceptor antibody. For instance, unusual residues may be changed to more frequently occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, RJ. Journal of Chromatography 705: 129-134, 1995).

In one embodiment the antibody heavy chain comprises a CH1 domain and the antibody light chain comprises a CL domain, either kappa or lambda.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or surface carries no net electrical charge. In one embodiment the antibody or fragment according to the present disclosure has an isoelectric point (pI) of at least 7. In one embodiment the antibody or fragment has an isoelectric point of at least 8, such as 8.5, 8.6, 8.7, 8.8 or 9. In one embodiment the pI of the antibody is 8. Programs such as ** ExPASY (Worldwide Website: expasy.ch/tools/pi_tool.html) (see Walker, The Proteomics Protocols Handbook, Humana Press (2005), 571-607) may be used to predict the isoelectric point of the antibody or fragment.

Antibodies for use in the invention may comprise at least one, at least two or all three heavy chain CDR sequences of SEQ ID NOS: 4 to 6 (HCDR1/HCDR2/HCDR3 respectively). These are the HCDR1/HCDR2/HCDR3 sequences of the Ab7326 antibody of the Examples as determined using Kabat methodology.

The Kabat and Chothia methods for determining CDR sequences are well known in the art (as well as other techniques). CDR sequences may be determined using any appropriate method and in the present invention, whilst Kabat is typically employed, other techniques could be used as well. In the present instance, SEQ ID NO: 3 presents the Ab7326 HCDR1 sequence as determined using a combined Chothia & Kabat definition.

Antibodies for use in the invention may comprise at least one, at least two or all three light chain CDR sequences of SEQ ID NOS: 7 to 9 (LCDR1/LCDR2/LCDR3 respectively). These are the LCDR1/LCDR2/LCDR3 sequences of Ab7326 using Kabat methodology.

In one embodiment, the antibody comprises at least a HCDR3 sequence of SEQ ID NO: 6.

Typically, the antibody comprises at least one heavy chain CDR sequence selected from SEQ ID NOS: 4 to 6 and at least one light chain CDR sequence selected from SEQ ID NOS 7 to 9. The antibody may comprise at least two heavy chain CDR sequences selected from SEQ ID NOS: 4 to 6 and at least two light chain CDR sequences selected from SEQ ID NOS: 7 to 9. The antibody typically comprises all three heavy chain CDR sequences of SEQ ID NOS: 4 to 6 (HCDR1/HCDR2/HCDR3 respectively) and all three light chain CDR sequences SEQ ID NOS: 7 to 9 (LCDR1/LCDR2/LCDR3 respectively). The antibodies may be chimeric, human or humanised antibodies.

The antibody may comprise a heavy chain variable region (HCVR) sequence of SEQ ID NO: 10 or 12 (the HCVR of Ab7326 variants 1 and 2). The antibody may comprise a light chain variable region (LCVR) sequence of SEQ ID NO: 11 or 13 (the LCVR of Ab7326 variants 1 and 2). The antibody preferably comprises the heavy chain variable region sequence of SEQ ID NO: 10 or 12 and the light chain variable region sequence of SEQ ID NO: 11 or 13 (especially HCVR/LVCR pairs of SEQ ID NOs: 10/11 or 12/13).

Ab7326 variants 1 and 2 differ by a single amino acid in the heavy chain variable region, and by a single amino acid in the light chain variable region, as follows:

Heavy chain variable region variant 1 has glutamic acid (E) at position 6. (SEQ ID NO:10) Heavy chain variable region variant 2 has glutamine (Q) at position 6. (SEQ ID NO:12)

Light chain variable region variant 1 has serine (S) at position 7. (SEQ ID NO:11)

Light chain variable region variant 2 has threonine (T) at position 7. (SEQ ID NO:13)

Thus, in one embodiment, the antibody comprises a heavy chain variable region (HCVR) sequence of SEQ ID NO: 10, wherein the glutamic acid residue at position 6 is substituted with a glutamine residue (E6Q); wherein the residue numbering is according to SEQ ID NO: 10.

In one embodiment, the antibody comprises a heavy chain variable region (HCVR) sequence of SEQ ID NO: 12, wherein the glutamine residue at position 6 is substituted with a glutamic acid residue (Q6E); wherein the residue numbering is according to SEQ ID NO: 12.

In one embodiment, the antibody comprises a light chain variable region (LCVR) sequence of SEQ ID NO: 11, wherein the serine residue at position 7 is substituted with a threonine residue (S7T); wherein the residue numbering is according to SEQ ID NO: 11.

In one embodiment, the antibody comprises a light chain variable region (LCVR) sequence of SEQ ID NO: 13, wherein the threonine residue at position 7 is substituted with a serine residue (T7S); wherein the residue numbering is according to SEQ ID NO: 13.

In one embodiment, the antibody comprises the sequence of SEQ ID NO: 3 or 4 for HCDR1, the sequence of SEQ ID NO: 5 for HCDR2, the sequence of SEQ ID NO: 6 for HCDR3, the sequence of SEQ ID NO: 7 for LCDR1, the sequence of SEQ ID NO: 8 for LCDR2 and the sequence of SEQ ID NO: 9 for LCDR3; and wherein the heavy chain variable region comprises a sequence having at least 95% identity, (e.g. at least 95%, 96%, 97%, 98% or 99% identity), to the sequence of SEQ ID NO: 10 and the light chain variable region comprises a sequence having at least 95% identity, (e.g. at least 95%, 96%, 97%, 98% or 99% identity), to the sequence of SEQ ID NO: 11.

In one embodiment, the antibody comprises the sequence of SEQ ID NO: 3 or 4 for HCDR1, the sequence of SEQ ID NO: 5 for HCDR2, the sequence of SEQ ID NO: 6 for HCDR3, the sequence of SEQ ID NO: 7 for LCDR1, the sequence of SEQ ID NO: 8 for LCDR2 and the sequence of SEQ ID NO: 9 for LCDR3; and wherein the heavy chain variable region comprises a sequence having at least 95% identity, (e.g. at least 95%, 96%, 97%, 98% or 99% identity), to the sequence of SEQ ID NO: 12 and the light chain variable region comprises a sequence having at least 95% identity, (e.g. at least 95%, 96%, 97%, 98% or 99% identity) to the sequence of SEQ ID NO: 13.

The antibody may comprise a heavy chain (H-chain) sequence of SEQ ID NO: 14 mouse full length IgG1 heavy chain variant 1, or SEQ ID NO: 28 mouse full length IgG1 heavy chain variant 2, or SEQ ID NO: 30 human full length IgG1 heavy chain variant 1, or SEQ ID NO: 16 human full length IgG1 heavy chain variant 2, or SEQ ID NO: 22 human full length IgG4P heavy chain variant 1, or SEQ ID NO: 34 human full-length IgG4P heavy chain variant 2, or SEQ ID NO: 18 Fab heavy chain variant 1, or SEQ ID NO: 32 Fab heavy chain variant 2.

The antibody may comprise a light chain (L-chain) sequence of SEQ ID NO: 15 mouse full length IgG1 light chain variant 1, or SEQ ID NO: 29 mouse full length IgG1 light chain variant 2, or SEQ ID NO: 31 human full length IgG1 light chain variant 1, or SEQ ID NO: 17 human full length IgG1 light chain variant 2, or SEQ ID NO: 23 human full length IgG4P light chain variant 1, or SEQ ID NO: 35 human full-length IgG4P light chain variant 2, or SEQ ID NO: 19 Fab light chain variant 1, or SEQ ID NO: 33 Fab light chain variant 2.

In one example, the antibody comprises a heavy chain/light chain sequence pair of SEQ ID NOs: 14/15 mouse full length IgG1 variant 1, or SEQ ID NOs: 28/29 mouse full length IgG1 variant 2, or SEQ ID NOs: 30/31 human full length IgG1 variant 1, or SEQ ID NOs: 16/17 human full length IgG1 variant 2, or SEQ ID NOs: 22/23 human full length IgG4P variant 1, or SEQ ID NOs: 34/35 human full-length IgG4P variant 2, or SEQ ID NOs: 18/19 Fab light chain variant 1, or SEQ ID NOs: 32/33 Fab light chain variant 2.

The variant forms of corresponding sequences may be interchanged. For example, the antibody may comprise a heavy chain/light chain sequence pair of SEQ ID NOs: 14/29 mouse full length IgG1 heavy chain variant 1/light chain variant 2, or SEQ ID NOs: 28/15 mouse full length IgG1 heavy chain variant 2/light chain variant 1, or SEQ ID NOs: 30/17 human full length IgG1 heavy chain variant 1/light chain variant 2, or SEQ ID NOs: 16/31 human full length IgG1 heavy chain variant 2/light chain variant 1, or SEQ ID NOs: 22/35 human full length IgG4P heavy chain variant 1/light chain variant 2, or SEQ ID NOs: 34/23 human full-length IgG4P heavy chain variant 2/light chain variant 1, or SEQ ID NOs: 18/33 Fab heavy chain variant 1/light chain variant 2, or SEQ ID NOs: 32/19 Fab heavy chain variant 2/light chain variant 1.

The antibodies may be chimeric, human or humanised antibodies.

The antibody may alternatively be or may comprise a variant of one of the specific sequences recited above. For example, a variant may be a substitution, deletion or addition variant of any of the above amino acid sequences.

A variant antibody may comprise 1, 2, 3, 4, 5, up to 10, up to 20 or more (typically up to a maximum of 50) amino acid substitutions and/or deletions from the specific sequences discussed above. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants typically involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

TABLE 1

| Amino acid properties. | |
|---|---|
| Ala | aliphatic, hydrophobic, neutral |
| Cys | polar, hydrophobic, neutral |
| Asp | polar, hydrophilic, charged (−) |
| Glu | polar, hydrophilic, charged (−) |
| Phe | aromatic, hydrophobic, neutral |
| Gly | aliphatic, neutral |
| His | aromatic, polar, hydrophilic, charged (+) |

TABLE 1-continued

Amino acid properties.

| | |
|---|---|
| Ile | aliphatic, hydrophobic, neutral |
| Lys | polar, hydrophilic, charged(+) |
| Leu | aliphatic, hydrophobic, neutral |
| Met | hydrophobic, neutral |
| Asn | polar, hydrophilic, neutral |
| Pro | hydrophobic, neutral |
| Gln | polar, hydrophilic, neutral |
| Arg | polar, hydrophilic, charged (+) |
| Ser | polar, hydrophilic, neutral |
| Thr | polar, hydrophilic, neutral |
| Val | aliphatic, hydrophobic, neutral |
| Trp | aromatic, hydrophobic, neutral |
| Tyr | aromatic, polar, hydrophobic |

"Derivatives" or "variants" generally include those in which instead of the naturally occurring amino acid the amino acid which appears in the sequence is a structural analog thereof. Amino acids used in the sequences may also be derivatized or modified, e.g. labelled, providing the function of the antibody is not significantly adversely affected.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

Variant antibodies may have an amino acid sequence which has more than about 60%, or more than about 70%, e.g. 75 or 80%, typically more than about 85%, e.g. more than about 90 or 95% amino acid identity to the amino acid sequences disclosed herein (particularly the HCVR/LCVR sequences and the H- and L-chain sequences). Furthermore, the antibody may be a variant which has more than about 60%, or more than about 70%, e.g. 75 or 80%, typically more than about 85%, e.g. more than about 90 or 95% amino acid identity to the HCVR/LCVR sequences and the H- and L-chain sequences disclosed herein, whilst retaining the exact CDRs disclosed for these sequences. Variants may retain at least about 90%, 91%, 92%, 93%, 94%, 95%, 96%, 97%, 98% or 99% identity to the HCVR/LCVR sequences and to the H- and L-chain sequences disclosed herein (in some circumstances whilst retaining the exact CDRs).

Variants typically retain about 60%—about 99% identity, about 80%—about 99% identity, about 90%—about 99% identity or about 95%—about 99% identity. This level of amino acid identity may be seen across the full length of the relevant SEQ ID NO sequence or over a part of the sequence, such as across about 20, 30, 50, 75, 100, 150, 200 or more amino acids, depending on the size of the full length polypeptide.

In connection with amino acid sequences, "sequence identity" refers to sequences which have the stated value when assessed using ClustalW (Thompson et al., 1994, supra) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatized.

Antibodies having specific sequences and derivatives and variants which maintain the function or activity of these chains are therefore provided for use in the present invention.

"Derivatives" as used herein is intended to include reactive derivatives, for example thiol-selective reactive groups such as maleimides. The reactive group may be linked directly or through a linker segment to a polymer. It will be appreciated that the residue of such a group will in some instances form part of the product as the linking group between the antibody fragment and the polymer.

The polymer may be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on a synthetic polymer include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly (ethyleneglycol) such as methoxypoly(ethyleneglycol) or derivatives thereof.

Specific naturally occurring polymers include lactose, amylose, dextran, glycogen or derivatives thereof.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues or extend circulating half-life (for review see Chapman, 2002, Advanced Drug Delivery Reviews, 54, 531-545). Thus, for example, where the product is intended to leave the circulation and penetrate tissue, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly (ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one example the antibody molecule is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Antibodies may compete for binding to Gremlin-1 with, or bind to the same epitope as, those defined above in terms of H-chain/L-chain, HCVR/LCVR or CDR sequences. In particular, an antibody may compete for binding to Gremlin-1 with, or bind to the same epitope as, an antibody which comprises a HCDR1/HCDR2/HCDR3/LCDR1/LCDR2/LCDR3 sequence combination of SEQ ID NOs: 4/5/6/7/8/9. An antibody may compete for binding to Gremlin-1 with, or bind to the same epitope as, an antibody which comprises a HCVR and LCVR sequence pair of SEQ ID NOs: 10/11 or 12/13 or full length chains of SEQ ID Nos: 14/15 or 16/17.

An "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

One can easily determine whether an antibody binds to the same epitope as, or competes for binding with, a reference antibody by using routine methods known in the art. For example, to determine if a test antibody binds to the same epitope as a reference antibody for use in the invention, the reference antibody is allowed to bind to a protein or peptide under saturating conditions. Next, the ability of a test antibody to bind to the protein or peptide is assessed. If the test antibody is able to bind to the protein or peptide following saturation binding with the reference antibody, it can be concluded that the test antibody binds to a different epitope than the reference antibody. On the other hand, if the test antibody is not able to bind to protein or peptide following saturation binding with the reference antibody, then the test antibody may bind to the same epitope as the epitope bound by the reference antibody of the invention.

To determine if an antibody competes for binding with a reference antibody, the above-described binding methodology is performed in two orientations. In a first orientation, the reference antibody is allowed to bind to a protein/peptide under saturating conditions followed by assessment of binding of the test antibody to the protein/peptide molecule. In a second orientation, the test antibody is allowed to bind to the protein/peptide under saturating conditions followed by assessment of binding of the reference antibody to the protein/peptide. If, in both orientations, only the first (saturating) antibody is capable of binding to the protein/peptide, then it is concluded that the test antibody and the reference antibody compete for binding to the protein/peptide. As will be appreciated by the skilled person, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50%, 75%, 90% or even 99% as measured in a competitive binding assay (see, e.g., Junghans et al., Cancer Res, 1990: 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

The anti-gremlin-1 antibody of the Examples, Ab7326, has been found to bind the following residues of Gremlin-1: Ile131, Lys147, Lys148, Phe149, Thr150, Thr151, Arg169, Lys174 and Gln175; where Lys147, Lys148, Phe149, Thr150, Thr151, Arg169, Lys174 and Gln175 are present on one Gremlin-1 monomer and Ile131 is present on the second Gremlin-1 monomer. The numbering is based on the UniProt entry O60565 of SEQ ID NO: 1. As discussed in the Examples section, these epitope residues were identified using NCONT analysis at 4 Å from the Gremlin-1-Ab7326 Fab complex.

Antibodies for use in the invention may therefore bind to an epitope which comprises at least one residue selected from Ile131, Lys147, Lys148, Phe149, Thr150, Thr151, Arg169, Lys174 and Gln175 (with residue numbering based on SEQ ID NO: 1). Antibodies for use in the invention may bind an epitope which comprises 2, 3, 4, 5, 6, 7, 8 or all 9 of these residues (preferably at least 5 residues).

Antibodies for use in the invention may also recognise an epitope where Ile131 is present on a different Gremlin-1 monomer to the other residues.

Although these residues are provided for a particular sequence of human Gremlin-1, the skilled person could extrapolate the positions of these residues to other corresponding Gremlin sequences using routine techniques. Antibodies binding to epitopes comprising the corresponding residues within these other Gremlin sequences are therefore also provided for use in the invention.

To screen for antibodies that bind to a particular epitope, a routine cross-blocking assay such as that described in Antibodies, Harlow and Lane (Cold Spring Harbor Press, Cold Spring Harb., NY) can be performed. Other methods include alanine scanning mutants, peptide blots (Reineke (2004) Methods Mol Biol 248:443-63), or peptide cleavage analysis. In addition, methods such as epitope excision, epitope extraction and chemical modification of antigens can be employed (Tomer (2000) Protein Science 9: 487-496). Such methods are well known in the art.

Antibody epitopes may also be determined by x-ray crystallography analysis. Antibodies for use in the present invention may therefore be assessed through x-ray crystallography analysis of the antibody bound to Gremlin-1. Epitopes may, in particular, be identified in this way by determining residues on Gremlin-1 within 4 Å of an antibody paratope residue.

Antibodies can be tested for binding to Gremlin-1 by, for example, standard ELISA or Western blotting. An ELISA assay can also be used to screen for hybridomas that show positive reactivity with the target protein. The binding selectivity of an antibody may also be determined by monitoring binding of the antibody to cells expressing the target protein, for example by flow cytometry. Thus, a screening method may comprise the step of identifying an antibody that is capable of binding Gremlin-1 by carrying out an ELISA or Western blot or by flow cytometry.

Antibodies may selectively (or specifically) recognise Gremlin-1. An antibody, or other compound, "selectively binds" or "selectively recognises" a protein when it binds with preferential or high affinity to the protein for which it is selective but does not substantially bind, or binds with low affinity, to other proteins. The selectivity of an antibody may be further studied by determining whether or not the antibody binds to other related proteins as discussed above or whether it discriminates between them. Antibodies for use in the invention typically recognise human Gremlin-1.

Antibodies may also have cross-reactivity for related proteins, or for human Gremlin-1 and for Gremlin-1 from other species.

By specific (or selective), it will be understood that the antibody binds to the protein of interest with no significant cross-reactivity to any other molecule. Cross-reactivity may be assessed by any suitable method described herein. Cross-reactivity of an antibody may be considered significant if the antibody binds to the other molecule at least about 5%, 10%, 15%, 20%, 25%, 30%, 35%, 40%, 45%, 50%, 55%, 60%, 65%, 70%, 75%, 80%, 85%, 90% or 100% as strongly as it binds to the protein of interest. An antibody that is specific (or selective) may bind to another molecule at less than about 90%, 85%, 80%, 75%, 70%, 65%, 60%, 55%, 50%, 45%, 40%, 35%, 30%, 25% or 20% the strength that it binds to the protein of interest. The antibody may bind to the other molecule at less than about 20%, less than about 15%, less than about 10% or less than about 5%, less than about 2% or less than about 1% the strength that it binds to the protein of interest.

Thus, antibodies suitable for use in the present invention may have a high affinity binding for (human) Gremlin-1. The antibody may have a dissociation constant ($K_D$) of less than <1 nM, and preferably <500 µM. In one example, the antibody has a dissociation constant ($K_D$) of less than 200 µM. In one example, the antibody has a dissociation constant ($K_D$) of less than 100 µM. A variety of methods can be used to determine the binding affinity of an antibody for its target antigen such as surface plasmon resonance assays, saturation assays, or immunoassays such as ELISA or RIA, as are well known to persons of skill in the art. An exemplary method for determining binding affinity is by surface plasmon resonance analysis on a BIAcore™ 2000 instrument (Biacore AB, Freiburg, Germany) using CM5 sensor chips, as described by Krinner et al., (2007) Mol. Immunol. February; 44 (5). 916-25, (Epub 2006 May 11).

The anti-Gremlin-1 antibody of the Examples, Ab7326, is an allosteric inhibitor of Gremlin-1 activity which binds to an epitope distal from the BMP binding site. (WO 2018/115017 A2) Ab7326 binds to Gremlin-1 with exceptionally high affinity with a Kd value <100 pM, and is expected to be particularly useful for use in the present invention.

An inhibitor of gremlin-1 activity may have an effect on any of the functions of Gremlin-1, but typically reduces binding of Gremlin-1 to BMP (BMP 2, 4, and/or 7). Gremlin-1 is a negative regulator of BMP and so reduced binding increases signalling through BMP.

BMP binding and signalling may be detected by any method known in the art. The Examples of the present application describe two functional assays for testing whether an agent reduces binding of gremlin-1 to BMP. Example 3 describes an Id1 reporter gene assay, where the Id1 gene is a target gene of BMP signalling. An increase in the signal in this assay may be used to determine if an agent reduces Gremlin-1 binding to BMP. Example 5 describes a SMAD phosphorylation assay. SMAD1, 5 and 8 are phosphorylated upon BMP signalling. An increase in SMAD phosphorylation may therefore be used to determine whether an agent reduces binding of Gremlin-1 to BMP.

Once a suitable antibody has been identified and selected, the amino acid sequence of the antibody may be identified by methods known in the art. The genes encoding the antibody can be cloned using degenerate primers. The antibody may be recombinantly produced by routine methods.

Examples of DNA sequences encoding full length heavy chains and light chains of Ab7326 are provided in the sequence listing:
SEQ ID NO: 24 (Human IgG1 heavy chain DNA variant 1)
SEQ ID NO: 25 (Human IgG1 light chain DNA variant 1)
SEQ ID NO: 26 (Human IgG4P heavy chain DNA variant 1)
SEQ ID NO: 27 (Human IgG4P light chain DNA variant 1).

Pharmaceutical Compositions, Dosages and Dosage Regimes

An inhibitor of gremlin-1 activity for use in the present invention may be provided in a pharmaceutical composition. The pharmaceutical composition will normally be sterile and will typically include a pharmaceutically acceptable carrier and/or adjuvant. A pharmaceutical composition for use in the invention may additionally comprise a pharmaceutically acceptable adjuvant and/or carrier.

The pharmaceutical compositions for use in the invention may include one or more pharmaceutically acceptable salts. A "pharmaceutically acceptable salt" refers to a salt that retains the desired biological activity of the parent molecule and does not impart any undesired toxicological effects. Examples of such salts include acid addition salts and base addition salts.

As used herein, "pharmaceutically acceptable carrier" includes any and all solvents, dispersion media, coatings, antibacterial and antifungal agents, isotonic and absorption delaying agents, and the like that are physiologically compatible. The carrier may be suitable for parenteral, e.g. intravenous, intramuscular, intradermal, intraocular, intraperitoneal, subcutaneous, spinal or other parenteral routes of administration, for example by injection or infusion. Alternatively, the carrier may be suitable for non-parenteral administration, such as a topical, epidermal or mucosal route of administration. The carrier may be suitable for oral administration. Depending on the route of administration, the inhibitor may be coated in a material to protect it from the action of acids and other natural conditions that may inactivate the inhibitor.

Pharmaceutically acceptable carriers comprise aqueous carriers or diluents. Examples of suitable aqueous carriers that may be employed in the pharmaceutical compositions for use in the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be desirable to include isotonic agents, for example, sugars, polyalcohols such as mannitol, sorbitol, or sodium chloride in the composition.

Pharmaceutical compositions typically must be sterile and stable under the conditions of manufacture and storage. The composition can be formulated as a solution, micro-emulsion, liposome, or other ordered structure suited to high drug concentration.

Pharmaceutical compositions for use in the invention may comprise additional active ingredients.

Also envisaged are kits comprising an inhibitor of gremlin-1 activity and instructions for use in a method of treatment according to the invention.

Agents for use in the invention or formulations or compositions thereof may be administered for therapeutic and/or prophylactic treatments.

In therapeutic applications, agents are administered to a subject already suffering from a disorder or condition, in an amount sufficient to cure, alleviate or partially arrest the condition or one or more of its symptoms. Such therapeutic treatment may result in a decrease in severity of symptoms, or an increase in frequency or duration of symptom-free periods. An amount adequate to accomplish this is defined as a "therapeutically effective amount".

In prophylactic applications, agents are administered to a subject at risk of a disorder or condition, in an amount sufficient to prevent or reduce the subsequent effects of the condition or one or more of its symptoms. An amount adequate to accomplish this is defined as a "prophylactically effective amount". Effective amounts for each purpose will depend on the severity of the disease or injury as well as the weight and general state of the subject.

A subject for administration may be a human or non-human animal. The term "non-human animal" includes all vertebrates, e.g., mammals and non-mammals, such as non-human primates, dogs, cats, horses, sheep, cows, chickens, amphibians, reptiles, etc. Administration to humans is typical.

An agent or pharmaceutical composition for use in the invention may be administered via one or more routes of administration using one or more of a variety of methods known in the art. As will be appreciated by the skilled artisan, the route and/or mode of administration will vary depending upon the desired results. Examples of routes of administration for agents or pharmaceutical compositions for use in the invention include parenteral routes, such as intravenous, intramuscular, intradermal, intraocular, intraperitoneal, subcutaneous, or spinal routes of administration, for example by injection or infusion. Alternatively, an agent or pharmaceutical composition can be administered via a non-parenteral route, such as a topical, epidermal or mucosal route of administration. The agent or pharmaceutical composition may be for oral administration.

A suitable dosage of an inhibitory agent or pharmaceutical composition for use in the invention may be determined by a skilled medical practitioner. Actual dosage levels of the active ingredients in the pharmaceutical compositions for use in the present invention may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions employed, the route of administration, the time of administration, the rate of excretion of the particular compound being employed, the duration of the treatment, the age, sex, weight, condition, general health and prior medical history of the patient being treated, and like factors well known in the medical arts.

A suitable dose may be, for example, in the range of from about 0.01 µg/kg to about 1000 mg/kg body weight, typically from about 0.1 µg/kg to about 100 mg/kg body weight, of the patient to be treated. For example, a suitable dosage may be from about 1 µg/kg to about 10 mg/kg body weight per day or from about 10 µg/kg to about 5 mg/kg body weight per day.

Dosage regimens may be adjusted to provide the optimum desired response (e.g., a therapeutic response). For example, a single dose may be administered, several divided doses may be administered over time or the dose may be proportionally reduced or increased as indicated by the therapeutic situation. Dosage unit form as used herein refers to physically discrete units suited as unitary dosages for the subjects to be treated; each unit contains a predetermined quantity of active agent calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the inhibitory agent in the patient and the duration of treatment desired.

Agents, formulations or pharmaceutical compositions for use in the invention may be co-administered with one or other more other therapeutic agents. Combined administration of two or more agents may be achieved in a number of different ways. Both may be administered together in a single composition, or they may be administered in separate compositions as part of a combined therapy. For example, the one may be administered before, after or concurrently with the other.

Therapeutic Indications

Inhibitors of gremlin-1 activity according to the present invention are provided for the treatment of a bone fracture or bone defect. A bone fracture is a break or crack in bone tissue and may be the result of a traumatic injury, such as a fall or impact, but can also occur as a result of diseases that affect bone integrity. A bone defect is a loss of bone, due to trauma or disease.

The fracture may be a fracture of any bone in the body.

The bone defect may be a bone defect in any bone of the body.

In one embodiment, the bone fracture is a delayed-union or non-union fracture. A delayed-union fracture is defined as a fracture which fails to reach union within 6-months post-fracture. A non-union fracture is defined as incomplete healing within 9 months, combined with a lack of radiological characteristics associated with fracture healing being observed over three consecutive months. (Einhorn et al; 2014; Buza et al; 2016). Examples of fractures that are that are prone to delayed-union or non-union development include tibia, distal radius, femoral neck and scaphoid.

In one embodiment, the bone fracture or bone defect occurs as a result of a disease that affects bone integrity. Examples of diseases that affect bone integrity include but are not limited to osteoporosis, osteogenesis imperfecta, diabetes, Paget's disease of bone, rheumatoid arthritis, ankylosing spondylitis, multiple myeloma, primary bone cancer (e.g. osteosarcoma, Ewing's sarcoma and chondrosarcoma), cancers that metastasise to the bone (e.g. breast cancer, prostate cancer and lung cancer), diffuse idiopathic skeletal hyperostosis, osteomyelitis, renal disease, Duchenne muscular dystrophy and thalassemia major.

FIGURES

Figure 5:
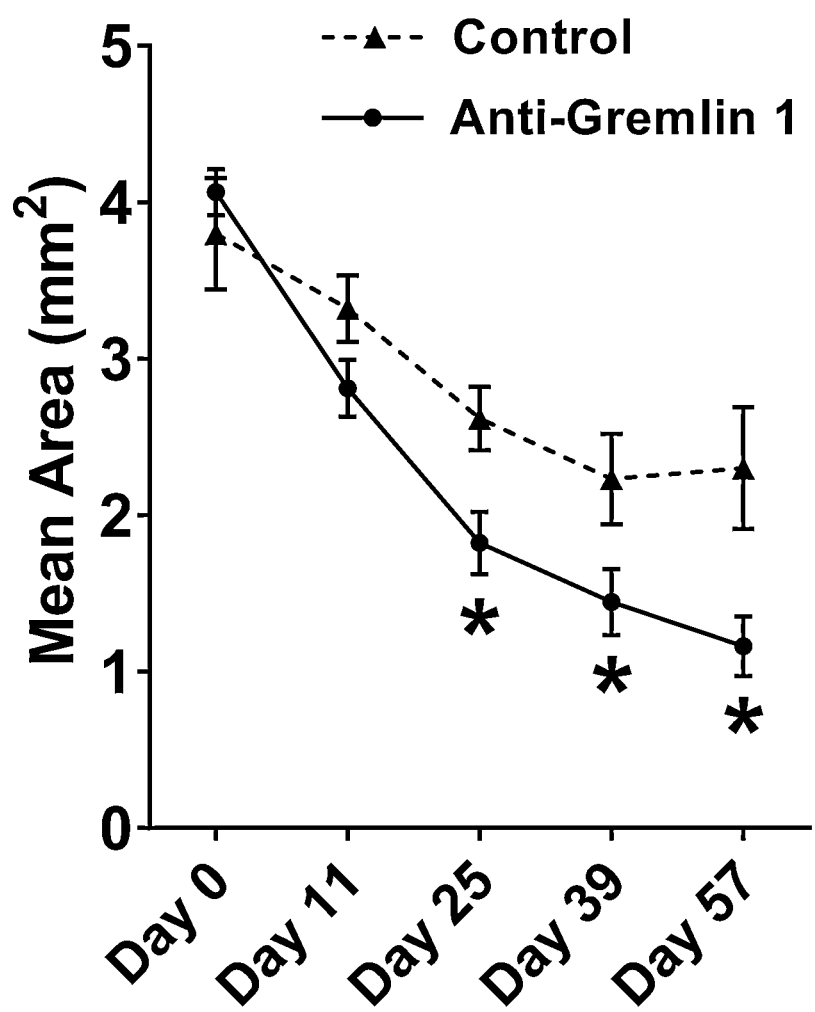

FIG. 5 shows examination of the area devoid of callus/bone tissue during fracture repair in acquired X-Ray images. The area within the defect, which was devoid of tissue, was quantified using definiens image analysis and subsequently compared between control and anti-gremlin 1 treated group. Results are presented as the mean±SD of 10 rats/group. *P<0.05; P<0.01; *P<0.001 as measured by Mann-Whitney U test.

Figure 6:
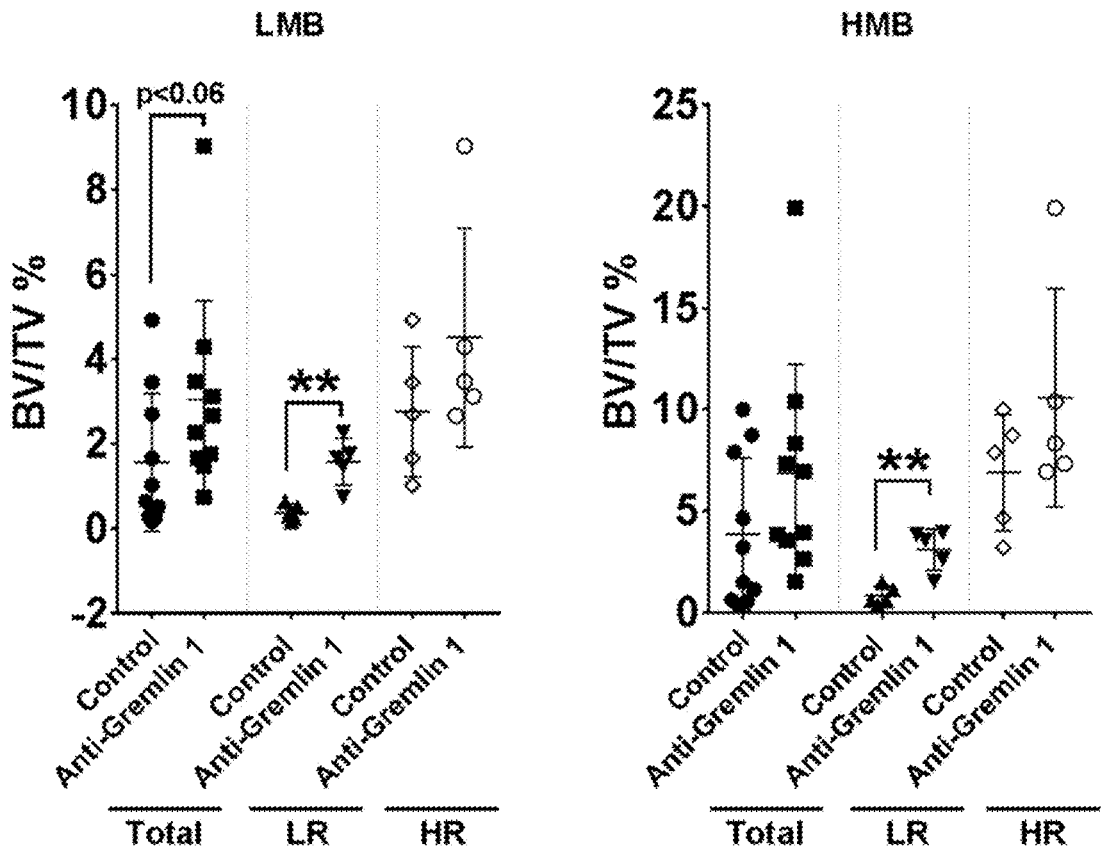
Figure 6:
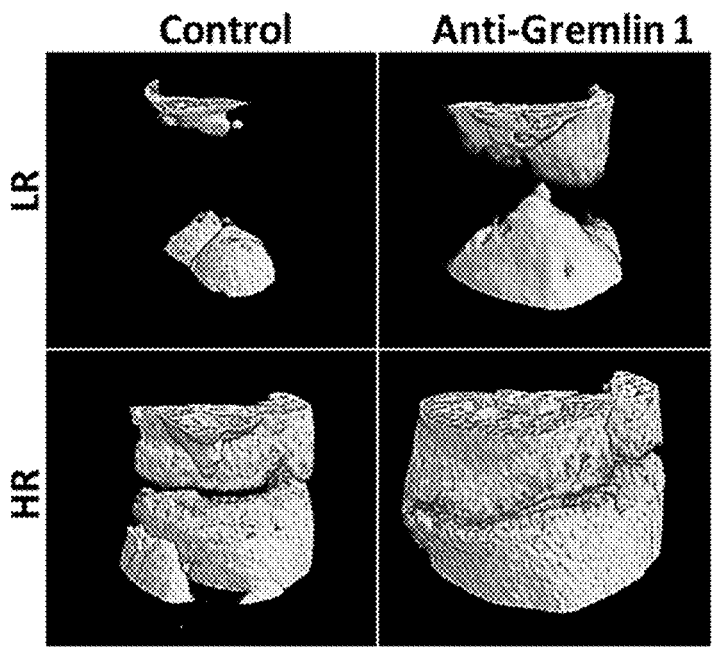

FIG. 6 shows examination of LMB (low mineral bone; newly formed bone) and HMB (high mineral bone; mature bone) within a 3 mm femoral bone defect. Panel A: 3D μCt analysis of femoral bone defect region to detect newly formed bone or mature bone. Percentage of bone volume/tissue volume was measured and compared all subjects (total) between control vs. treatments with anti-gremlin 1. Comparisons between control versus anti-gremlin 1 treated group in animals separated as low responders (LR-incomplete bridging) and high responders (HR complete bridging) were also performed. Results are presented as the mean±SD. *P<0.05; P<0.01; *P<0.001 as measured by Mann-Whitney U test. Panel B: representative μCt illustrating the 3D bone volume renderings of LR and HR groups in control and after anti-gremlin 1 treatment.

Figure 7:
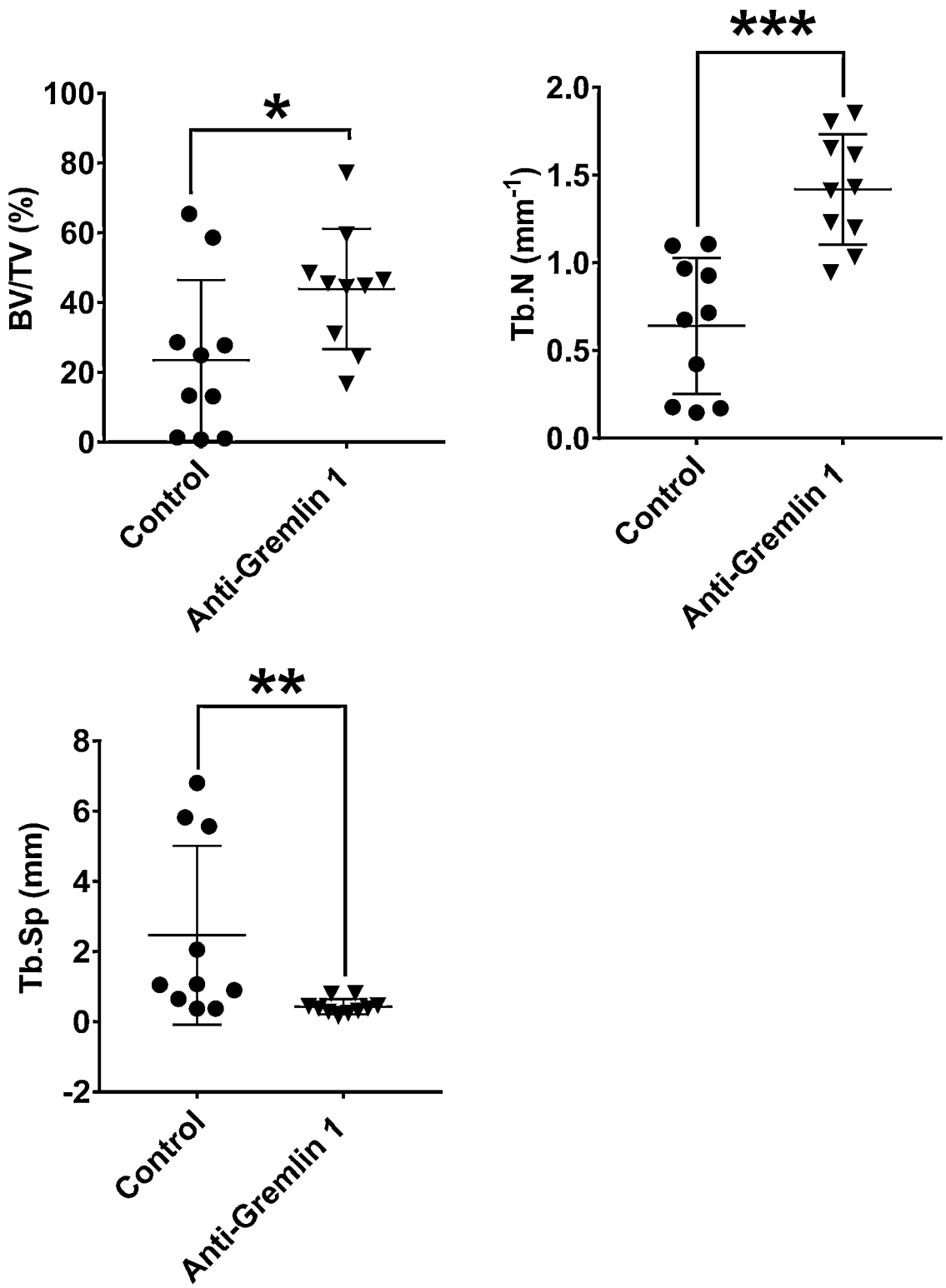

FIG. 7 shows histomorphometric analysis of femoral bone defect. Percentage of bone volume/tissue volume (BV/TV (%)), trabecular number (Tb.N) and trabecular separation (Tb.Sp) was compared between control versus anti-gremlin 1 treated group. Results are presented as the mean±SD of 10 rats/group. *P<0.05; P<0.01; *P<0.001 as measured by Mann-Whitney U test.

Figure 8:
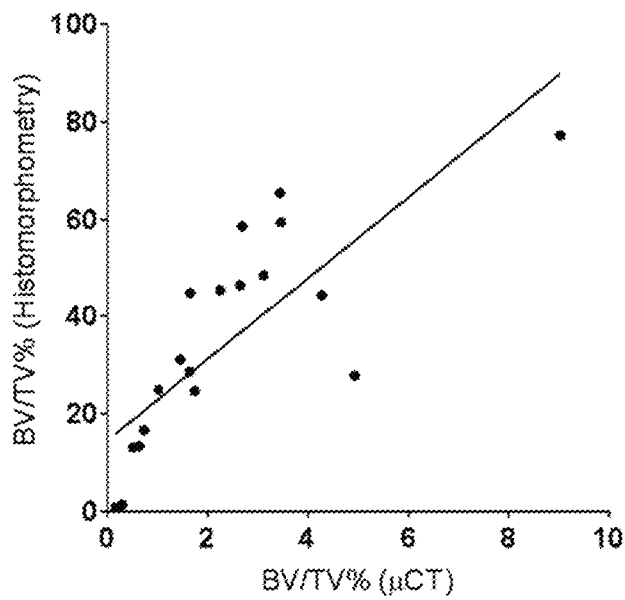
Figure 8:
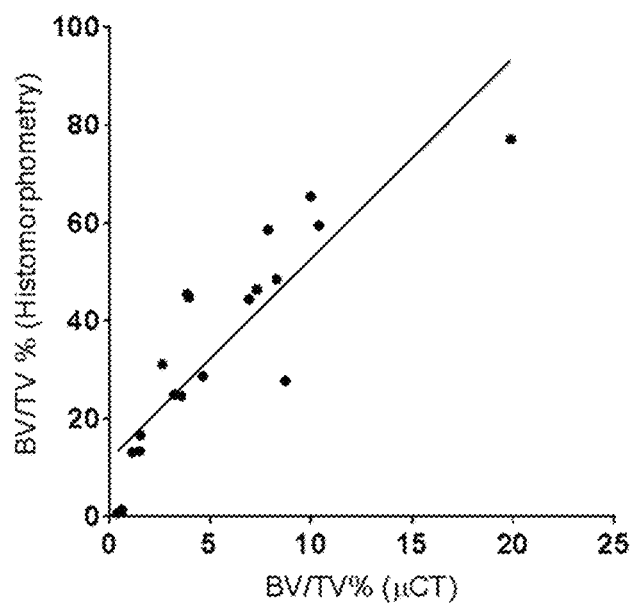

FIG. 8 shows correlation of 3D μCT analysis and 2D histomorphometry analysis of total BV/TV %. Correlations were performed in both groups on LMB (low mineral bone; newly formed bone) and HMB (high mineral bone; mature bone) within a 3 mm femoral bone defect and compared to 2D histomorphometry score data (n=20). The Pearson's score indicates significant correlation of BV/TV % between 3D μCT analysis and 2D histomorphometry analysis.

The following Examples illustrate the invention.

EXAMPLES

Example 1—Protein Expression, Purification, Refolding and Structure Determination Protein Expression and Inclusion Body Preparation A truncated human Gremlin-1 coding sequence (SEQ ID NO: 20), optimised for expression in *E. coli*, was cloned into a modified pET32a vector (Merck Millipore) using BamHI/XhoI, generating a vector encoding the Gremlin sequence with an N-terminal 6His-TEV tag (pET-hGremlin1).

Expressed sequence: MGSSHHHHHHSSGEN-LYFQGSAMPGEEVLESSQEALHVTERKYLKRDWCK-TQPLKQTIHE EGCNSRTIINRFCYGQCNSFYIPRHIR-KEEGSFQSCSFCKPKKFTTMMVTLNCPELQPPTKK KRVTRVKQCRCISIDLD; SEQ ID NO: 2 (with non-Gremlin residues of the 6His-TEV tag shown in italics). Sequence numbering based on UniProt O60565 & SEQ ID NO: 1.

The pET-hGremlin1 plasmid DNA was used to transform BL21(DE3) cells. A single ampicillin resistant colony was picked from a LB/Amp agar plate and used to inoculate a 100 ml starter culture of LB/Amp. After shaking (200 rpm) for 16 hr at 37° C., 25 ml of the starter culture was used to inoculate 500 mL of 2×TY/Amp media. The culture was shaken (250 rpm) at 37° C. until an $OD_{600}$ of 3 was achieved. Subsequently, the culture was supplemented with 20 mL of a MOPS+glycerol feed mix (1M MOPS pH 7.4, 40% glycerol, 0.5% $MgSO_4$, 0.42% $MgCl_2$), induced with 300 μM IPTG and further incubated at 17° C., 180 rpm for 16 hours. Cells were harvested in a centrifuge (4,000 g for 20 minutes at 4° C.).

Cell pellets were resuspended in Lysis Buffer (PBS pH 7.4, 0.35 mg/ml lysozyme, 10 μg/ml DNase and 3 mM $MgCl_2$) at 4° C. and the insoluble fraction was harvested by centrifugation at 3,500 g for 30 minutes at 4° C. Pelleted inclusion bodies were washed three times by resuspending in wash buffer (50 mM Tris, 500 mM NaCl, 0.5% Triton X-100, pH 8.0), followed by centrifugation at 21,000 g for 15 minutes. An additional two washes were performed using wash buffer without Triton X-100.

Solubilisation

Inclusion bodies were resuspended in denaturing buffer (8 M Urea, 100 mM Tris, 1 mM EDTA, 10 mM $Na_2S_4O_6$ and 100 mM $Na_2SO_3$, pH 8.5), stirred for 16 hrs at room-temperature and clarified by centrifugation at 21,000 g for 15 minutes.

Pre-Refolding Purification

The solubilized inclusion bodies were loaded onto a Sephacryl S-200 26/60 column (120 mL) equilibrated in 8 M Urea, 50 mM MES, 200 mM NaCl, 1 mM EDTA, pH 6.0. Fractions containing Gremlin-1 protein were diluted with 6 M Urea, 20 mM MES, pH 6.0 and loaded onto HiTrap SP HP cation exchange columns and eluted with a 1 M NaCl gradient over 10 column volumes (10 CVs). Fractions containing purified, denatured hGremlin-1 protein were pooled.

Refolding

Denatured purified Gremlin-1 protein was added dropwise to re-folding buffer (50 mM Tris, pH 8.5, 150 mM NaCl, 5 mM GSH and 5 mM GSSG, 0.5 mM Cysteine, 5 mM EDTA, 0.5 M Arginine) to a final concentration of 0.1 mg/ml and incubated at 4° C. with constant stirring for 5 days. After 5 days the Gremlin-1 protein was dialysed against 20 mM HEPES, 100 mM NaCl, pH 7.5.

Following dialysis protein was applied to heparin HiTrap column and eluted using a gradient of 0-100% heparin elution buffer (20 mM HEPES, 1 M NaCl, pH 7.5) over 20 CV. Correctly folded protein eluted at 1 M NaCl whereas any misfolded protein eluted at lower salt concentrations.

Protein eluting at 1 M NaCl was concentrated and purified further on a S75 26/60 column equilibrated with 20 mM Hepes, pH 7.5, 1 M NaCl.

Protein was characterised by SDS PAGE (shift in gel), demonstrated to have the expected molecular weight and correct arrangement of disulphide bonds using liquid chromatography mass spectrometry (LC-MS) and to be active in a cell assay (ID1 reporter assay).

Gremlin 1 Structure Determination

Gremlin 1 protein crystals were grown using the hanging-drop method by mixing a solution of Gremlin 1 at 6.6 mg/ml and 0.1 M citric acid at pH 4, 1 M lithium chloride and 27% polyethylene glycol (PEG) 6000 in a 1:1 ratio. Before data collection, crystals were cryo-protected by adding 20% glycerol to the crystallization buffer. Diffraction data were collected at the Diamond Light Source and were processed using XDS (Kabsch, Wolfgang (2010) Acta Crystallographica Section D 66, 125-132). Diffraction data statistics are summarized in the table below:

TABLE 2

Diffraction data statistics

| Diffraction Statistics | |
| --- | --- |
| Wavelength (Å) | 0.97949 |
| Space group | C2 |
| Cell dimensions | a = 84.55 Å, |
|  | b = 107.22 Å, |
|  | c = 77.09 Å; |
|  | α = 90.00°, |
|  | β = 120.43°, |
|  | γ = 90.00° |
| Resolution range* (Å) | 26.19-2.72 ( 2.79-2.72) |
| Completeness (%) | 98.5 (99.0) |
| Multiplicity | 3.4 (3.4) |
| I/sigma | 9.6 (2.0) |
| Rmerge | 0.095 (0.622) |
| Refinement Statistics | |
| Resolution Range (Å) | 26.19-2.72 |
| $R_{cryst}$ | 0.24 |
| $R_{free}$ | 0.29 |
| R.m.s.d. bonds (Å)** | 0.013 |
| R.m.s.d. angles (°) | 1.782 |

*values in parenthesis correspond to the highest resolution shell
** r.m.s.d root mean square deviation Gremlin-1 structure was solved by molecular replacement using Phaser (McCoy et al, J Appl Cryst (2007), 40, 658-674) and a Gremlin-1 model available from proprietary Gremlin-1/Fab complex coordinates. The resultant model of Gremlin-1 contained four copies of Gremlin 1 monomer organised as two dimers. Model corrections were made with Coot (Emsley et al Acta Crystallographica Section D: Biological Crystallography 66 (4), 486-501) and coordinates were refined using Refmac (Murshudov et al REFMAC5 for the refinement of macromolecular crystal structures. Acta Crystallographica Section D: Biological Crystallography. 2011; 67 (Pt 4):355-367). Final coordinates were validated with Molprobity (Chen et al. (2010) MolProbity: all-atom structure validation for macromolecular crystallography. Acta Crystallographica D66:12-21). A summary of model refinement statistics is shown in Table 2 above.

Example 2—BMP Binding Residues on Gremlin-1

As discussed above, Gremlin-1 belongs to the bone morphogenic protein (BMP) antagonist protein family within a sub-group known as the DAN family. Within the DAN family, Gremlin-1 shares greatest homology with Gremlin-2 (PRDC).

The 2.7 Å human Gremlin-1 structure resolved in Example 1 shares many features in common with the published mouse Gremlin-2 structure (Nolan et al (2013), Structure, 21, 1417-1429). The overall fold is very similar, with two copies of Gremlin-1 forming an antiparallel, non-covalent dimer, arranged in an arch. Each monomer adopts the characteristic finger-wrist-finger arrangement with a cystine-knot motif towards the wrist end, opposite the fingers. Sequence identity between the proteins is 52% rising to 67% within the sequence visible in the two structures. The most highly conserved region lies in the extensive dimer interface where all the key contact residues are 100% conserved.

Residues involved in BMP's 2, 4 & 7 binding to mouse Gremlin-2 (PRDC) and DAN (NBL1) have been identified using mutagenesis (Nolan et al (2013), Structure, 21, 1417-1429 and Nolan et al (2014) J. Biol. Chem. 290, 4759-4771). The predicted BMP binding epitope encompasses a hydrophobic patch spanning across both monomers on the convex surface of the dimer. Six residues were identified by mutagenesis; Trp72, Phe96, Tyr98, Phe104, Tyr105 & Phe117 and are 100% conserved in human Gremlin-1 (numbering based on the mouse Gremlin-2 sequence). The degree of homology extends to the positioning of the side chains which adopt an identical conformation in both proteins.

The amino acid numbering used in the Gremlin PDB file matches the numbering in the published mouse Gremlin-2 structure based on a structural alignment. This enables like for like comparison of amino acids when describing the structures. However, for clarity the key residues identified as playing a role in BMP binding are shown below with numbering based on the PDB file and UniProt file of SEQ ID NO: 1 in brackets: Trp72(93), Phe96(117), Tyr98(119), Phe104(125), Tyr105(126) & Phe117(138).

In both mouse Gremlin-2 and human Gremlin-1 the hydrophobic BMP binding epitope is partially buried by an alpha helix formed by the N-terminal residues of each protein. A model of BMP binding has been proposed whereby the N-terminus can flex, exposing the full BMP binding interface (Nolan et al (2013), Structure, 21, 1417-1429). In the present analysis, the N-terminal residues were removed from the human Gremlin-1 and mouse Gremlin-2 structures before rendering a surface to reveal the similarity of the BMP binding faces on each protein.

The literature only describes mutagenesis of six resides that have an effect on BMP binding. It is possible that the actual BMP epitope covers a larger surface area, encompassing neighbouring amino acids. By highlighting all residues, within 6 Å of those mutated, on the surface of Gremlin-1, a larger region of Gremlin-1 is revealed that could potentially be targeted by a therapeutic. This more extensive region encompasses the following amino acids of human Gremlin-1:

Asp92-Leu99
Arg116-His130
Ser137-Ser142
Cys176-Cys178
(Numbering based on SEQ ID NO: 1)

By combining published information with the crystal structure information of human Gremlin-1, regions of human Gremlin-1 that offer themselves as a potential route for therapeutic intervention blocking its interaction with BMP's have been identified.

Example 3—Hek Id1 Reporter Gene Assay

Background

The Hek Id1 reporter gene assay uses Clone 12 Hek293-Id1 reporter cells. This cell line was stably transfected with Id1 transcription factor. Id1 is a transcription factor in the BMP signalling pathway. Gremlin is known to bind BMPs prevent binding to their receptors reducing the luciferase signal from the reporter gene. Therefore, using this reporter assay, it is possible to screen anti-Gremlin antibodies and see if there are any that block the interaction of Gremlin with BMPs. A restoration of the luciferase signal is seen in these cells if there is a blocking of this interaction.

Method

Clone 12 cells were cultured in DMEM containing 10% FCS, 1× L-Glutamine & 1× NEAA. Cells are also grown in the presence of Hygromycin B (200 μg/ml) to ensure cells do not lose Id1 gene expression. Cells were assayed in DMEM containing 0.5% FCS, 1× L-Glutamine & 1× NEAA. Hygromycin B is not needed for the short time that the cells are in the assay.

The cells were washed in PBS, lifted off using cell dissociation buffer, spun and counted before being seeded at 5×10$^4$/well in 70 µl (Density of 7.14×10$^5$/ml). Plates used were white, opaque Poly-D-Lysine coated 96-well sterile. Cells go in incubator for about 3-4 hours to settle down. BMP heterodimers were reconstituted to 200 µg/ml in 4 mM HCL. BMP was diluted to 10 µg/ml in assay media using a glass vial to give a new working stock.

In a polypropylene plate, Gremlin-1 was diluted 1:2 for an 8 point dose response curve with a top final dose of 1 µg/ml.

An additional volume of 20 µl media was added per well and plates were incubated at 37° C. for 45 mins.

BMP prepared at 100× was added to all wells except wells containing cells only. All wells are made up to 60 µl with assay medium and incubated for a further 45 mins at 37° C.

Post incubation, 30 µl of sample was transferred per well of assay plate and incubated for 20-24 hours before measuring luminescence signal.

Cell Steady Glo was thawed in advance at room temperature. Assay plates were cooled to room temperature for about 10-15 mins before adding the reagent. Luciferase signal was detected by addition of cell steady glo reagent (100 µl) for 20 minutes on shaker at room temperature and measuring luminescence using cell titre glo protocol on Synergy 2.

The maximum signal was generated from wells containing BMP and the minimum signal was generated from the wells containing cells only.

Results

Gremlin-1 full length and truncated forms were tested in the Hek-Id1 reporter gene assay to confirm the blocking activity against BMP4/7.

The percentage of inhibition from dose response assays was calculated based on the maximum and minimum signals in the assay and the data fitted using 4 parameter logistical fit. The IC$_{50}$ was calculated based on the inflexion point of the curve.

Table 3: Potency results for full length Gremlin-1 and truncated Gremlin-1 in the Hek-Id1 reporter gene assay.

Conclusion

Gremlin 1 was able to inhibit the BMP 4/7 signalling in the Hek-Id1 reporter gene assay.

Example 4—Production of Anti-Gremlin-1 Antibodies

Anti-Gremlin-1 antibodies were derived by immunisation using purified gremlin-1 as described in Example 1, and by library panning. The library was generated in-house as a naïve human library with the V-regions amplified from blood donations.

Immunisation yielded 26 distinct antibodies binding Gremlin-1 from the first round of immunisation. These antibodies were scaled up and purified for testing in screening assays.

25 human and mouse cross-reactive antibodies from the library were panned using recombinant human Gremlin from R&D Systems. 10 antibodies were selected for scale up and purified as scFvs for testing in the screening assays.

Example 5—Screening of Anti-Gremlin-1 Antibodies

Antibodies were screened using the Hek-Id1 reporter gene assay described in Example 3 and by measuring SMAD phosphorylation. SMAD1, 5 and 8 are phosphorylated upon BMP signalling. Inhibitors of Gremlin-1 therefore increase SMAD phosphorylation.

SMAD phosphorylation assays were conducted on A549 cells or on human lung fibroblasts. Phosphorylation levels were determined using MSD.

Results

Figure 1:
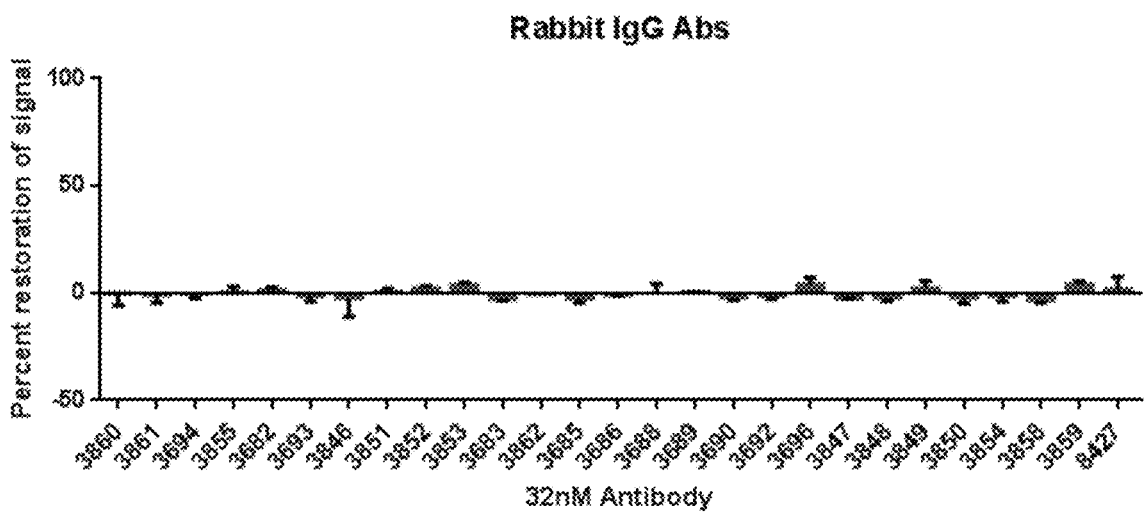
FIG. 1 shows percentage restoration of signal for the immunisation derived antibodies in the HEK-ID1 reporter gene assay.

In the Hek-Id1 reporter gene assay, there were no apparent hits with the immunisation derived antibodies (with a 10 fold excess of antibody tested against a BMP4/7 heterodimer). Results are shown in FIG. 1.

Figure 2:
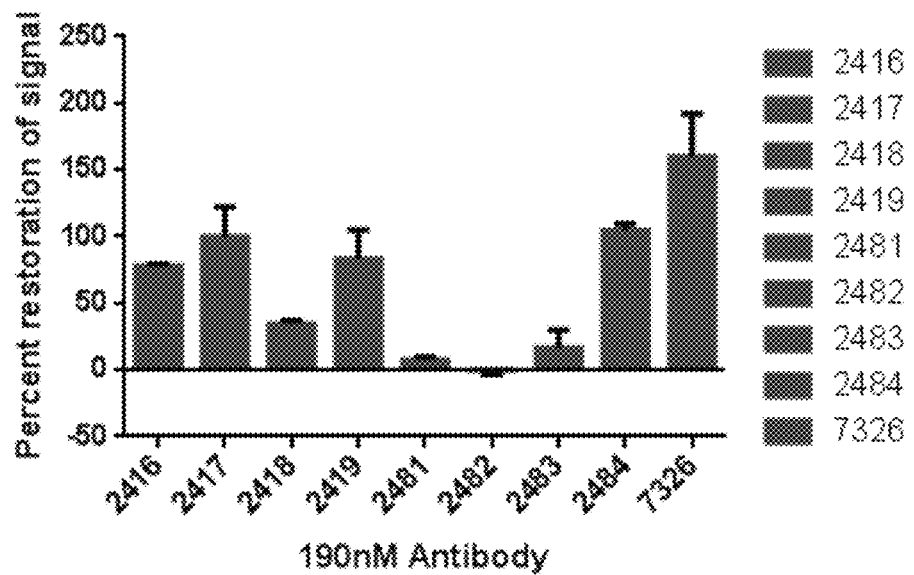
FIG. 2 shows percentage restoration of signal for library derived antibodies in the HEK-ID1 reporter gene assay.

In contrast, a number of library derived antibodies were capable of restoring signal in the Hek-Id1 reporter gene assay (50-fold excess of antibodies with a 50% gremlin dose) (FIG. 2). Of these, Ab2416 and Ab2417 contained high levels of endotoxin. Ab7326 maintained blocking ability at a 10-fold excess and 80% inhibition Gremlin-1 concentration.

Figures 3A, 3B:
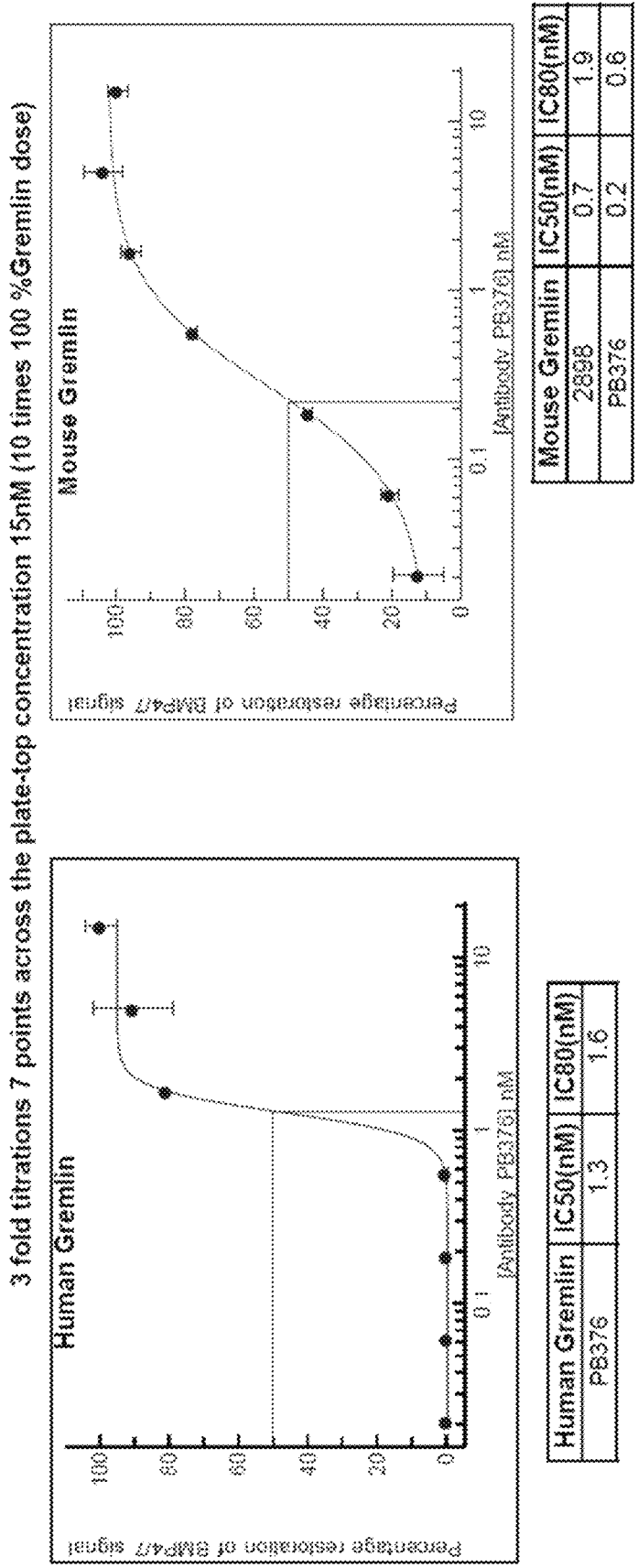
FIGS. 3A-3B show results for the HEK-ID1 reporter gene assay with titrations of human Gremlin (FIG. 3A) and mouse Gremlin (FIG. 3B) and the effect of antibody 7326 (shown as antibody PB376) in restoring signalling of BMP.

Additional results are presented in FIGS. 3A (human gremlin) and 3B (mouse Gremlin). These Figures show titrations of Ab7326 (labelled as PB376) up to 15 nM. Ab7326 was shown to restore signalling of BMP when blocked by either human (IC$_{50}$ of 1.3 nM) or mouse (IC$_{50}$ of 0.2 nM Gremlin). The antibody functions both as a human and mouse IgG1.

Sequences of the mouse and human full length IgG1 are presented below. In order to synthesise the mouse and human full length IgG1 proteins, the Ab7326 variable regions derived from the library were re-cloned into vectors comprising the appropriate antibody constant domains.

Because Ab7326 came from a naïve human library, where Abs are cloned as scFvs, in order to re-clone the 7326 variable regions as full length Abs or Fabs, it was necessary to PCR amplify the VH and VK using pools of primers/degenerate primers. The amplified PCR products were then digested and cloned simultaneously into mouse and human vectors. As the VH and VK were amplified by pools of primers/degenerate primers, two variant forms of the products were obtained, differing by a single amino acid residue derived from subtly different primers annealing during the PCR process.

The two variant forms of heavy chain variable region differed by a single amino acid at position 6, and the two variant forms of the light chain variable region differed by a single amino acid at position 7, as shown below:

Heavy chain variable region variant 1 has glutamic acid (E) at position 6.
Heavy chain variable region variant 2 has glutamine (Q) at position 6.
Light chain variable region variant 1 has serine (S) at position 7.
Light chain variable region variant 2 has threonine (T) at position 7.

```
Mouse full length IgG1 - heavy chain variant 1
                                    (SEQ ID NO: 14)
QVQLVESGAE VKKPGATVKI SCKVSGYTFT DYYMHWVQQA

PGKGLEWMGL VDPEDGETIY AEKFQGRVTI TADTSTDTAY

MELSSLRSED TAVYYCATDA RGSGSYYPNH FDYWGQGTLV

TVSSAKTTPP SVYPLAPGSA AQTNSMVTLG CLVKGYFPEP

VTVTWNSGSL SSGVHTFPAV LQSDLYTLSS SVTVPSSTWP

SETVTCNVAH PASSTKVDKK IVPRDCGCKP CICTVPEVSS
```

-continued

```
VFIFPPKPKD VLTITLTPKV TCVVVDISKD DPEVQFSWFV

DDVEVHTAQT QPREEQFNST FRSVSELPIM HQDWLNGKEF

KCRVNSAAFP APIEKTISKT KGRPKAPQVY TIPPPKEQMA

KDKVSLTCMI TDFFPEDITV EWQWNGQPAE NYKNTQPIMD

TDGSYFVYSK LNVQKSNWEA GNTFTCSVLH EGLHNHHTEK

SLSHSPGK
```

Mouse full length IgG1 - light chain variant 1
(SEQ ID NO: 15)
```
DIVMTQSPDS LAVSLGERAT INCKSSQSVL YSSNNKNYLA

WYQQKPGQPP KLLIYWASTR ESGVPDRFSG SGSGTDFTLT

INSLQAEDVA VYFCQQYYDT PTFGQGTRLE IKRTDAAPTV

SIFPPSSEQL TSGGASVVCF LNNFYPKDIN VKWKIDGSER

QNGVLNSWTD QDSKDSTYSM SSTLTLTKDE YERHNSYTCE

ATHKTSTSPI VKSFNRNEC
```

Mouse full length IgG1 - heavy chain variant 2
(SEQ ID NO: 28)
```
QVQLVQSGAE VKKPGATVKI SCKVSGYTFT DYYMHWVQQA

PGKGLEWMGL VDPEDGETIY AEKFQGRVTI TADTSTDTAY

MELSSLRSED TAVYYCATDA RGSGSYYPNH FDYWGQGTLV

TVSSAKTTPP SVYPLAPGSA AQTNSMVTLG CLVKGYFPEP

VTVTWNSGSL SSGVHTFPAV LQSDLYTLSS SVTVPSSTWP

SETVTCNVAH PASSTKVDKK IVPRDCGCKP CICTVPEVSS

VFIFPPKPKD VLTITLTPKV TCVVVDISKD DPEVQFSWFV

DDVEVHTAQT QPREEQFNST FRSVSELPIM HQDWLNGKEF

KCRVNSAAFP APIEKTISKT KGRPKAPQVY TIPPPKEQMA

KDKVSLTCMI TDFFPEDITV EWQWNGQPAE NYKNTQPIMD

TDGSYFVYSK LNVQKSNWEA GNTFTCSVLH EGLHNHHTEK

SLSHSPGK
```

Mouse full length IgG1 - light chain variant 2
(SEQ ID NO: 29)
```
DIVMTQTPDS LAVSLGERAT INCKSSQSVL YSSNNKNYLA

WYQQKPGQPP KLLIYWASTR ESGVPDRFSG SGSGTDFTLT

INSLQAEDVA VYFCQQYYDT PTFGQGTRLE IKRTDAAPTV

SIFPPSSEQL TSGGASVVCF LNNFYPKDIN VKWKIDGSER

QNGVLNSWTD QDSKDSTYSM SSTLTLTKDE YERHNSYTCE

ATHKTSTSPI VKSFNRNEC
```

Human full length IgG1 - heavy chain variant 1
(SEQ ID NO: 30)
```
QVQLVESGAE VKKPGATVKI SCKVSGYTFT DYYMHWVQQA

PGKGLEWMGL VDPEDGETIY AEKFQGRVTI TADTSTDTAY

MELSSLRSED TAVYYCATDA RGSGSYYPNH FDYWGQGTLV

TVSSASTKGP SVFPLAPSSK STSGGTAALG CLVKDYFPEP

VTVSWNSGAL TSGVHTFPAV LQSSGLYSLS SVVTVPSSSL

GTQTYICNVN HKPSNTKVDK KVEPKSCDKT HTCPPCPAPE

LLGGPSVFLF PPKPKDTLMI SRTPEVTCVV VDVSHEDPEV

KFNWYVDGVE VHNAKTKPRE EQYNSTYRVV SVLTVLHQDW

LNGKEYKCKV SNKALPAPIE KTISKAKGQP REPQVYTLPP

SRDELTKNQV SLTCLVKGFY PSDIAVEWES NGQPENNYKT

TPPVLDSDGS FFLYSKLTVD KSRWQQGNVF SCSVMHEALH

NHYTQKSLSL SPGK
```

Human full length IgG1 - light chain variant 1
(SEQ ID NO: 31)
```
DIVMTQSPDS LAVSLGERAT INCKSSQSVL YSSNNKNYLA

WYQQKPGQPP KLLIYWASTR ESGVPDRFSG SGSGTDFTLT

INSLQAEDVA VYFCQQYYDT PTFGQGTRLE IKRTVAAPSV

FIFPPSDEQL KSGTASVVCL LNNFYPREAK VQWKVDNALQ

SGNSQESVTE QDSKDSTYSL SSTLTLSKAD YEKHKVYACE

VTHQGLSSPV TKSFNRGEC
```

Human full length IgG1 - heavy chain variant 2
(SEQ ID NO: 16)
```
QVQLVQSGAE VKKPGATVKI SCKVSGYTFT DYYMHWVQQA

PGKGLEWMGL VDPEDGETIY AEKFQGRVTI TADTSTDTAY

MELSSLRSED TAVYYCATDA RGSGSYYPNH FDYWGQGTLV

TVSSASTKGP SVFPLAPSSK STSGGTAALG CLVKDYFPEP

VTVSWNSGAL TSGVHTFPAV LQSSGLYSLS SVVTVPSSSL

GTQTYICNVN HKPSNTKVDK KVEPKSCDKT HTCPPCPAPE

LLGGPSVFLF PPKPKDTLMI SRTPEVTCVV VDVSHEDPEV

KFNWYVDGVE VHNAKTKPRE EQYNSTYRVV SVLTVLHQDW

LNGKEYKCKV SNKALPAPIE KTISKAKGQP REPQVYTLPP

SRDELTKNQV SLTCLVKGFY PSDIAVEWES NGQPENNYKT

TPPVLDSDGS FFLYSKLTVD KSRWQQGNVF SCSVMHEALH

NHYTQKSLSL SPGK
```

Human full length IgG1 - light chain variant 2
(SEQ ID NO: 17)
```
DIVMTQTPDS LAVSLGERAT INCKSSQSVL YSSNNKNYLA

WYQQKPGQPP KLLIYWASTR ESGVPDRFSG SGSGTDFTLT

INSLQAEDVA VYFCQQYYDT PTFGQGTRLE IKRTVAAPSV

FIFPPSDEQL KSGTASVVCL LNNFYPREAK VQWKVDNALQ

SGNSQESVTE QDSKDSTYSL SSTLTLSKAD YEKHKVYACE

VTHQGLSSPV TKSFNRGEC
```

Antibody CDRs were determined using the Kabat method (highlighted in bold in the above sequences). Additional HCDR1 residues using the Chothia definition are in italics. Constant region sequences are underlined.

Restoration of p-SMAD signalling with anti-Gremlin 1 antibodies is shown in Table 4 below.

TABLE 4

Restoration of p-SMAD signalling

|  | 2417 | 2418 | 2419 | 2481 | 2482 | 2483 | 2484 | 7326 | 8427 |
|---|---|---|---|---|---|---|---|---|---|
| BMP 2 50 ng/ml | 109.1% +/- 2.8% | 58.2% +/- 1.9% | 32.6% +/- 1.4% | 40.4% +/- 0.6% | 35.3% +/- 0.8% | 43.1% +/- 2.1% | 104.0% +/- 2.7% | 107.2% +/- 3.5% | 51.3% +/- 1.4% |
| BMP 4 25 ng/ml | 109.6% +/- 3.0% | 71.3% +/- 3.1% | 31.7% +/- 1.2% | 60.1% +/- 2.2% | 54.4% +/- 1.3% | 72.5% +/- 2.1% | 105.2% +/- 3.3% | 110.0% +/- 3.8% | 78.2% +/- 2.5% |
| BMP 7 200 ng/ml | 111.5% +/- 3.8% | 99.5% +/- 3.2% | 53.8% +/- 3.4% | 64.4% +/- 1.3% | 52.3% +/- 1.1% | 66.2% +/- 1.2% | 105.2% +/- 4.3% | 108.0% +/- 3.2% | 72.6% +/- 2.5% |
| BMP-2/7 50 ng/ml | 119.3% +/- 2.6% | 78.6% +/- 3.6% | 50.8% +/- 2.7% | 53.7% +/- 3.1% | 47.6% +/- 1.5% | 56.1% +/- 2.5% | 120.4% +/- 4.4% | 128.5% +/- 2.9% | 62.8% +/- 2.5% |
| BMP4/7 50 ng/ml | 113.7% +/- 3.1% | 78.0% +/- 4.0% | 61.4% +/- 4.0% | 48.3% +/- 2.1% | 41.7% +/- 1.7% | 50.8% +/- 1.7% | 112.4% +/- 2.5% | 127.0% +/- 3.1% | 63.3% +/- 2.1% |

Results are shown as a percentage of SMAD phosphorylation by BMP alone (control BMP). Experiments were performed using lung fibroblasts from idiopathic pulmonary fibrosis patients. rhGremlin-1 and the anti-Gremlin-1 antibodies were preincubated for 45 minutes at room temperature. rhGremlin-1 and the anti-Gremlin-1 antibodies were then added with BMP to the cells for 30 minutes.

Table 5 then shows further results in the SMAD phosphorylation assay, where displacement of BMP-2 or BMP4/7 from Gremlin 1-BMP complexes by anti-Gremlin-1 antibodies was investigated. Experiments were again performed using lung fibroblasts from idiopathic pulmonary fibrosis patients. rhBMP-2 or rhBMP 4/7 were preincubated with rhGremlin-1 for 1 hour at room temperature. The BMP-2- or BMP4/7-Gremlin-1 complexes were incubated with different concentrations of the anti-Gremlin-1 antibodies overnight at 4° C. Antibody concentrations represent the final concentration on the plate.

TABLE 5

Displacement of BMP-2 or BMP4/7 from Gremlin 1-BMP complexes by anti-Gremlin-1 antibodies

|  |  | 81.3 µg/ml | 40.6 µg/ml | 20.3 µg/ml | 10.2 µg/ml | 5.1 µg/ml | 2.55 µg/ml | 1.27 µg/ml | 0.63 µg/ml |
|---|---|---|---|---|---|---|---|---|---|
| 2484 | BMP 2 50 ng/ml | 100.3% +/- 3.5% | 98.8% +/- 2.7% | 97.0% +/- 2.9% | 93.5% +/- 2.6% | 86.4% +/- 2.0% | 79.9% +/- 1.9% | 66.5% +/- 2.8% | 54.8% +/- 0.3% |
| 2484 | BMP4/7 50 ng/ml | 136.4% +/- 4.2% | 133.2% +/- 1.0% | 121.4% +/- 1.4% | 108.1% +/- 4.9% | 86.6% +/- 4.4% | 74.7% +/- 2.2% | 65.8% +/- 0.6% | 60.7% +/- 1.5% |
| 7326 | BMP 2 50 ng/ml | 103.7% +/- 1.1% | 101.5% +/- 2.4% | 99.4% +/- 3.8% | 103.8% +/- 2.4% | 100.3% +/- 2.2% | 103.2% +/- 4.3% | 102.8% +/- 2.8% | 97.0% +/- 2.9% |
| 7326 | BMP4/7 50 ng/ml | 133.7% +/- 0.8% | 132.3% +/- 1.8% | 130.3% +/- 4.2% | 125.6% +/- 10.0% | 121.4% +/- 4.2% | 120.9% +/- 3.3% | 111.1% +/- 2.3% | 102.0% +/- 4.5% |

The results shown in Table 5 demonstrate that Ab7326 can displace already complexed BMP-2 or BMP4/7 from Gremlin 1-BMP complexes. Ab7326 can achieve this displacement at much lower concentrations that the comparison antibody 2484. This provides evidence that Ab7326 is an allosteric inhibitor, consistent with our finding that the binding site for Ab7326 is distal from the known BMP binding regions on gremlin-1. Thus Ab7326 is able to access the allosteric binding site even when BMP is complexed to gremlin-1, resulting in significantly improved inhibition of gremlin activity.

Example 6—Obtaining the Crystal Structure of Gremlin-1 in Complex with the 7326 Fab The crystal structure of human Gremlin-1 in complex with Ab7326 Fab was solved at a resolution of 2.1 Å. Fab sequences are shown below:

Heavy chain:
SEQ ID NO: 18
QVQLVESGAEVKKPGATVKISCKVSGYTFTDYYMHWVQQAPGKGLEWMGL

VDPEDGETIYAEKFQGRVTITADTSTDTAYMELSSLRSEDTAVYYCATDA

RGSGSYYPNHFDYWGQGTLVTVSSASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSC

-continued

Light chain:
SEQ ID NO: 19
DIVMTQSPDSLAVSLGERATINCKSSQSVLYSSNNKNYLAWYQQKPGQPP

KLLIYWASTRESGVPDRFSGSGSGTDFTLTINSLQAEDVAVYFCQQYYDT

PTFGQGTRLEIKRTVAAPSVFIFPPSDEQLKSGTASVVCLLNNFYPREAK

-continued

VQWKVDNALQSGNSQESVTEQDSKDSTYSLSSTLTLSKADYEKHKVYACE

VTHQGLSSPVTKSFNRGEC

The CCP4 software NCONT was then used to identify all contacts at 4 Å between Gremlin-1 and the Fab. The following residues were identified: Ile131, Lys147, Lys148, Phe149, Thr150, Thr151, Arg169, Lys174 and Gln175 (numbering based on the UniProt Sequence of SEQ ID NO: 1 (numbered as Ile110, Lys126, Lys127, Phe128, Thr129, Thr130, Arg148, Lys153 and Gln154 in the structure file which matches the numbering of mouse Gremlin-2).

Figure 4:
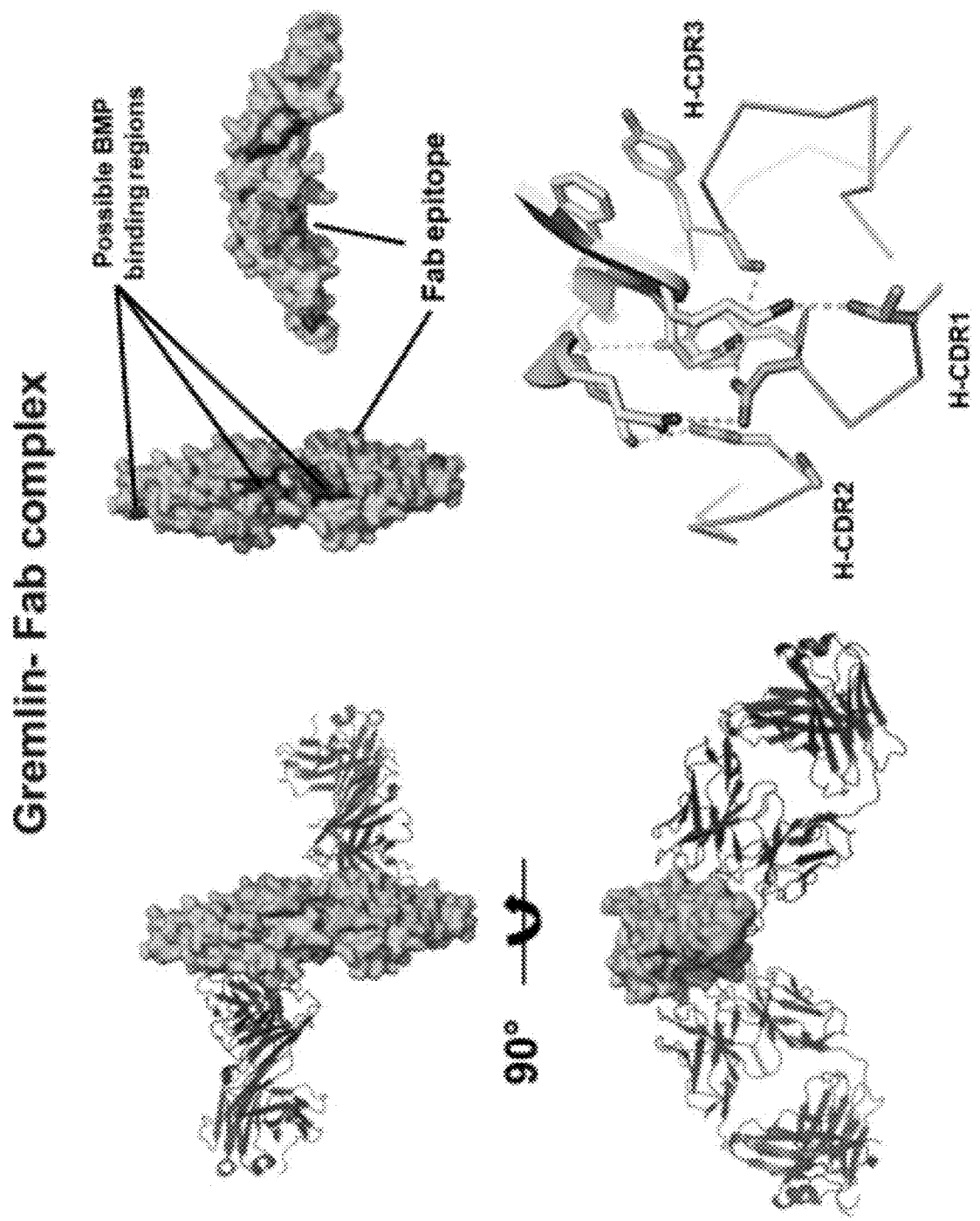
FIG. 4 shows a structural model of the Gremlin-Fab complex, with the possible BMP binding regions and the Fab epitope highlighted.

FIG. 4 shows structural models of the Gremlin-Fab complex, with the Fab epitope residues shown relative to the BMP binding regions.

Ab7326 is an inhibitory antibody which acts allosterically, i.e. it binds away from the BMP binding regions.

Example 7—Affinity Measurements for Binding of Anti-Gremlin-1 Antibody Ab7326 to Gremlin-1

Method

The affinity of anti-Gremlin mIgG for human Gremlin 1 was determined by biomolecular interaction analysis using surface plasmon resonance (SPR) technology on a Biacore T200 system, GE Healthcare Bio-Sciences AB. Anti-Gremlin mIgG was captured by an immobilised anti-mouse Fc surface and Gremlin 1 was titrated over the captured mIgG.

The capture ligand (affinipure F(ab')$_2$ fragment of goat anti-mouse IgG, Fc fragment specific, 115-006-071, Jackson ImmunoResearch Inc.) was immobilised at 50 μg/ml in 10 mM NaAc, pH5.0 on flow cell 2 of a CM4 Sensor Chip via amine coupling chemistry, using 600 s activation and deactivation injections, to a level of ~1600 response units (RU). HBS-EP+ buffer (0.01 M HEPES pH 7.4, 0.15 M NaCl, 3 mM EDTA, 0.05% Surfactant P20) was used as the running buffer with a flow rate of 10 μl/min. A reference surface was prepared on flow cell 1 by activating and deactivating the surface as for flow cell 2 but omitting the capture ligand.

The assay buffer was HBS-EP+ plus an extra 150 mM NaCl to give a final NaCl concentration of 300 mM plus 1% CMD40. A 60 s injection of anti-Gremlin mIgG (at 5 μg/ml in running buffer) was passed over flow cells 1 and 2 to give a capture level of approximately 100 RU on the immobilised anti-mouse IgG, Fc surface. Recombinant human Gremlin 1 was titrated in running buffer from 5 nM (using 2-fold dilutions) and injected over flow cells 1 and 2 at a flow rate of 30 μl/min for 3 min followed by a 5 min dissociation phase. A buffer only control was also included. The surface was regenerated at a flow rate of 10 μl/min by a 60 s injection of 50 mM HCl, a 30 s injection of 5 mM NaOH and a 30 s injection of 50 mM HCl.

The kinetic data was determined using Biacore T200 evaluation software. The affinity measurements were made at 25° C.

Results

Binding affinity, taken as the average $K_D$ value for 5 determinations, was found to be below 100 μM.

Example 8. Inhibition of Gremlin-1 Activity Accelerates Healing and Bridging in an in Vivo Model of Bone Fracture Repair 8.1. Materials and Methods Rat Fracture Model and Drug Administration Long bone segmental defect models have been widely used for the research of bone healing and regeneration (Sato et al; 2014). In the present study, a 3 mm femoral defect was created in 10-week old male rats and stabilised using an 8-hole PEEK plate (RIS. 602.105, RISystem, Switzerland). The plate was fixed to the bone with a forceps in the middle of the diaphysis, before the bone was drilled and fixed with screws. A 3 mm fracture gap was created using a 0.44 mm Gigly saw. The defect size/consistency/fixation was quality controlled by X-Ray imaging using Faxitron (MX-20-DC5, Faxitron Bioptics LLC, USA), this time point was defined as Day 0.

Weekly dosing was commenced on Day 1 for a period of 8 weeks as outlined in Table 1.

X-ray images were subsequently acquired during the in-life phase of the study at day 11, 25, 39 and 57 in order to assess the callus formation and the progress of healing. Definiens image analysis was utilized to quantify the area of the defect that was devoid of bone tissue in the captured X-Ray images.

TABLE 6

Treatment Groups.

| Group | Animal Number | Treatment | Dose | Dosing Regimen | Time |
|---|---|---|---|---|---|
| 1 | 10 | Vehicle | Vehicle: 1 ml, s.c. | Once/week | Total of 57 days |
| 2 | 10 | Anti-Gremlin-1 | 30 mg/kg, 1 ml, s.c. | Once/week | |

Micro-CT Analysis of Fracture Healing

Femora (fractured side) were scanned at 17.2 μm resolution using micro-CT (SkyScan 1076). A region of approximately 15 mm of the callus with the fracture in the centre was acquired. The scans were reconstructed using the Skyscan NRECON software (1.7.10) and then the reconstructed slices were further segmented to exclude fixator pins at a 3 mm defined region calculated from the mid-point of the femoral fracture defect.

Histomorphometric analysis of fracture callus in 3D was performed by SkyScan software (v. 1.13.1). The mid-point within the 3 mm femoral fracture defect was determined and slices 1.5 mm distal and proximal to the mid-point were segmented for each limb measured. Subsequently, the binarization of the reconstructed datasets and segmentation were performed following two defined thresholds, one to delineate the low mineralized callus (thus quantifying newly formed bone) and the other one to define mature bone. Further segmentation of these data was carried out on femora of animals classified as low responders based on satisfying the criteria of incomplete bridging of the femoral defect or high responders exhibiting bridging of the fracture site.

Histomorphometry Analysis of Fracture

Femora were fixed in 10% neutral-buffered formalin for 24 h, dehydrated and embedded in methyl methacrylate (MMA) at low temperature. 50-μm-thick sections were stained with Toluidine Blue to quantify the bone elements of the healing gap defect. Histomorphometric parameters were measured on the trabecular bone of the fracture defect site. Measurements were performed through image analysis.

Statistical Analysis

The results were presented as mean values±SD. Statistical analysis was performed using a two-tailed Mann Whitney U test with GraphPad Prism software unless otherwise stated.

8.2 Results

Analysis of X-Ray images obtained during the in-life phase of the study indicated that the anti-gremlin-1 antibody accelerated fracture healing with the control and treated groups significantly diverging after 25 days ($P<0.05$). This effect was apparent for the remainder of the study (FIG. 5).

Micro-CT analysis of terminal samples revealed that treatment with anti-gremlin-1 antibody (30 mg/kg/once weekly) led to an increase in newly formed bone within the fracture callus site ($P=0.06$).

The incidence of fracture non-union in this model is approximately 60% with no intervention (Sato et al; 2014). To test whether gremlin-1 inhibition reduced the incidence of non-union development, the animals were classified as low responders (LR) and high responders (HR). Gremlin-1 inhibition resulted in a significant increase in the percentage of bone volume/tissue volume (BV/TV %) within LMB (low mineral bone; newly formed bone) ($P<0.01$) and HMB (high mineral bone; mature bone) ($P<0.01$) in the low responder group compared to controls, thus indicating progressive repair of the cohort likely to form non-union.

Additionally, there was a trend (non-significant) towards increased LMB and HMB BV/TV % in the high responder group in response to anti-gremlin-1 treatment (FIG. 6A, representative images of LR and HR are shown in FIG. 6B).

Two-dimensional histomorphometric analysis of bone parameters was performed on histological sections of the fracture site (FIG. 7). Treatment with anti-gremlin-1 antibody significantly increased percentage of bone volume/tissue volume (BV/TV %) ($P<0.05$) compared to control. Anti-gremlin-1 significantly increased trabecular number (Tb.N) ($P<0.001$) and significantly decreased trabecular separation (Tb.Sp) ($P<0.01$) indicating increased trabecular bone due to treatment with anti-gremlin-1.

Correlations were performed between two-dimensional histomorphometric analysis and three-dimensional μCT analysis by comparing the LMB and HMB groups segmented in μCt analysis and the two-dimensional histomorphometry analysis of fracture sections (FIG. 8).

Comparisons measured by Pearson's correlation revealed a positive and significant correlation between histomorphometry and μCT analysis in the LMB ($P<0.0001$) and HMB groups ($P<0.0001$) thus validating the data from each dataset.

8.3. Conclusion

Inhibition of gremlin-1 activity using a neutralising anti-gremlin-1 antibody resulted in accelerated fracture repair, with significant differences between control and treated groups evident after 25 days (3 doses of antibody). Additionally, terminal analysis of the fracture site indicated the enhanced formation of bone tissue in the low responder animals, which otherwise would likely form non-union. Therefore, inhibition of gremlin-1 activity is a promising therapy for the prevention or treatment of non-union fractures and may be of particular value for the treatment of fractures that are prone to non-union development, for example, tibia, distal radius, femoral neck and scaphoid.

SEQUENCE LISTING

```
SEQUENCE LISTING
(Human Gremlin-1; Uniprot ID: O60565)
                                                        SEQ ID NO: 1
MSRTAYTVGALLLLLGTLLPAAEGKKKGSQGAIPPPDKAQHNDSEQTQSPQQPGSRNRGRG

QGRGTAMPGEEVLESSQEALHVTERKYLKRDWCKTQPLKQTIHEEGCNSRTIINRFCYGQC

NSFYIPRHIRKEEGSFQSCSFCKPKKFTTMMVTLNCPELQPPTKKKRVTRVKQCRCISIDL

D (Human truncated Gremlin-1 used in
crystallography with N-terminal tag)
                                                        SEQ ID NO: 2
MGSSHHHHHHSSGENLYFQGSAMPGEEVLESSQEALHVTERKYLKRDWCKTQPLKQTIHEE

GCNSRTIINRFCYGQCNSFYIPRHIRKEEGSFQSCSFCKPKKFTTMMVTLNCPELQPPTKK

KRVTRVKQCRCISIDLD (Ab7326 HCDR1 combined Kabat & Chothia)
                                                        SEQ ID NO: 3
GYTFTDYYMH (Ab7326 HCDR1 Kabat)
                                                        SEQ ID NO: 4
DYYMH (Ab7326 HCDR2 Kabat)
                                                        SEQ ID NO: 5
LVDPEDGETIYAEKFQG (Ab7326 HCDR3 Kabat)
                                                        SEQ ID NO: 6
DARGSGSYYPNHFDY
```

-continued (Ab7326 LCDR1 Kabat)
SEQ ID NO: 7
KSSQSVLYSSNNKNYLA (Ab7326 LCDR2 Kabat)
SEQ ID NO: 8
WASTRES (Ab7326 LCDR3 Kabat)
SEQ ID NO: 9
QQYYDTPT (Ab7326 Heavy chain variable region variant 1)
SEQ ID NO: 10
QVQLVESGAEVKKPGATVKISCKVSGYTFTDYYMHWVQQAPGKGLEWMGLVDPEDGETIYA
EKFQGRVTITADTSTDTAYMELSSLRSEDTAVYYCATDARGSGSYYPNHFDYWGQGTLVTV
SS (Ab7326 Light chain variable region variant 1)
SEQ ID NO: 11
DIVMTQSPDSLAVSLGERATINCKSSQSVLYSSNNKNYLAWYQQKPGQPPKLLIYWASTRE
SGVPDRFSGSGSGTDFTLTINSLQAEDVAVYFCQQYYDTPTFGQGTRLEIK (Ab7326 Heavy chain variable region variant 2)
SEQ ID NO: 12
QVQLVQSGAEVKKPGATVKISCKVSGYTFTDYYMHWVQQAPGKGLEWMGLVDPEDGETIYA
EKFQGRVTITADTSTDTAYMELSSLRSEDTAVYYCATDARGSGSYYPNHFDYWGQGTLVTV
SS (Ab7326 Light chain variable region variant 2)
SEQ ID NO: 13
DIVMTQTPDSLAVSLGERATINCKSSQSVLYSSNNKNYLAWYQQKPGQPPKLLIYWASTRE
SGVPDRFSGSGSGTDFTLTINSLQAEDVAVYFCQQYYDTPTFGQGTRLEIK (Mouse full length IgG1 heavy chain variant 1)
SEQ ID NO: 14
QVQLVESGAEVKKPGATVKISCKVSGYTFTDYYMHWVQQAPGKGLEWMGLVDPEDGETIYA
EKFQGRVTITADTSTDTAYMELSSLRSEDTAVYYCATDARGSGSYYPNHFDYWGQGTLVTV
SSAKTTPPSVYPLAPGSAAQTNSMVTLGCLVKGYFPEPVTVTWNSGSLSSGVHTFPAVLQS
DLYTLSSSVTVPSSTWPSETVTCNVAHPASSTKVDKKIVPRDCGCKPCICTVPEVSSVFIF
PPKPKDVLTITLTPKVTCVVVDISKDDPEVQFSWFVDDVEVHTAQTQPREEQFNSTFRSVS
ELPIMHQDWLNGKEFKCRVNSAAFPAPIEKTISKTKGRPKAPQVYTIPPPKEQMAKDKVSL
TCMITDFFPEDITVEWQWNGQPAENYKNTQPIMDTDGSYFVYSKLNVQKSNWEAGNTFTCS
VLHEGLHNHHTEKSLSHSPGK (Mouse full length IgG1 light chain variant 1)
SEQ ID NO: 15
DIVMTQSPDSLAVSLGERATINCKSSQSVLYSSNNKNYLAWYQQKPGQPPKLLIYWASTRE
SGVPDRFSGSGSGTDFTLTINSLQAEDVAVYFCQQYYDTPTFGQGTRLEIKRTDAAPTVSI
FPPSSEQLTSGGASVVCFLNNFYPKDINVKWKIDGSERQNGVLNSWTDQDSKDSTYSMSST
LTLTKDEYERHNSYTCEATHKTSTSPIVKSFNRNEC (Human full length IgG1 heavy chain variant 2)
SEQ ID NO: 16
QVQLVQSGAEVKKPGATVKISCKVSGYTFTDYYMHWVQQAPGKGLEWMGLVDPEDGETIYA
EKFQGRVTITADTSTDTAYMELSSLRSEDTAVYYCATDARGSGSYYPNHFDYWGQGTLVTV
SSASTKGPSVFPLAPSSKSTSGGTAALGCLVKDYFPEPVTVSWNSGALTSGVHTFPAVLQS
SGLYSLSSVVTVPSSSLGTQTYICNVNHKPSNTKVDKKVEPKSCDKTHTCPPCPAPELLGG
PSVFLFPPKPKDTLMISRTPEVTCVVVDVSHEDPEVKFNWYVDGVEVHNAKTKPREEQYNS -continued

TYRVVSVLTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVDKSRWQQG

NVFSCSVMHEALHNHYTQKSLSLSPGK (Human full length IgG1 light chain variant 2)

SEQ ID NO: 17

DIVMTQTPDSLAVSLGERATINCKSSQSVLYSSNNKNYLAWYQQKPGQPPKLLIYWASTRE

SGVPDRFSGSGSGTDFTLTINSLQAEDVAVYFCQQYYDTPTFGQGTRLEIKRTVAAPSVFI

FPPSDEQLKSGTASVVCLLNNFYPREAKVQWKVDNALQSGNSQESVTEQDSKDSTYSLSST

LTLSKADYEKHKVYACEVTHQGLSSPVTKSFNRGEC (Fab heavy chain variant 1)

SEQ ID NO: 18

QVQLVESGAEVKKPGATVKISCKVSGYTFTDYYMHWVQQAPGKGLEWMGLVDPEDGETIYA

EKFQGRVTITADTSTDTAYMELSSLRSEDTAVYYCATDARGSGSYYPNHFDYWGQGTLVTV

SSASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSC (Fab light chain variant 1)

SEQ ID NO: 19

DIVMTQSPDSLAVSLGERATINCKSSQSVLYSSNNKNYLAWYQQKPGQPPKLLIYWASTRE

SGVPDRFSGSGSGTDFTLTINSLQAEDVAVYFCQQYYDTPTFGQGTRLEIKRTVAAPSVFI

FPPSDEQLKSGTASVVCLLNNFYPREAKVQWKVDNALQSGNSQESVTEQDSKDSTYSLSST

LTLSKADYEKHKVYACEVTHQGLSSPVTKSFNRGEC (Human truncated Gremlin-1 used in
crystallography without N-terminal tag)

SEQ ID NO: 20

AMPGEEVLESSQEALHVTERKYLKRDWCKTQPLKQTIHEEGCNSRTIINRFCYGQCNSFYI

PRHIRKEEGSFQSCSFCKPKKFTTMMVTLNCPELQPPTKKKRVTRVKQCRCISIDLD (Mature Gremlin-1 sequence of SEQ ID NO: 1
lacking the signal peptide of amino acids 1-21)

SEQ ID NO: 21

KKKGSQGAIPPPDKAQHNDSEQTQSPQQPGSRNRGRGQGRGTAMPGEEVLESSQEALHVTE

RKYLKRDWCKTQPLKQTIHEEGCNSRTIINRFCYGQCNSFYIPRHIRKEEGSFQSCSFCKP

KKFTTMMVTLNCPELQPPTKKKRVTRVKQCRCISIDLD (Human IgG4P heavy chain variant 1)

SEQ ID NO: 22

QVQLVESGAEVKKPGATVKISCKVSGYTFTDYYMHWVQQAPGKGLEWMGLVDPEDGETIYA

EKFQGRVTITADTSTDTAYMELSSLRSEDTAVYYCATDARGSGSYYPNHFDYWGQGTLVTV

SSASTKGPSVFPLAPCSRSTSESTAALGCLVKDYFPEPVTVSWNSGALTSGVHTFPAVLQS

SGLYSLSSVVTVPSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRLTVDKSRWQEGNVF

SCSVMHEALHNHYTQKSLSLSLGK (Human IgG4P light chain variant 1)

SEQ ID NO: 23

DIVMTQSPDSLAVSLGERATINCKSSQSVLYSSNNKNYLAWYQQKPGQPPKLLIYWASTRE

SGVPDRFSGSGSGTDFTLTINSLQAEDVAVYFCQQYYDTPTFGQGTRLEIKRTVAAPSVFI

FPPSDEQLKSGTASVVCLLNNFYPREAKVQWKVDNALQSGNSQESVTEQDSKDSTYSLSST

LTLSKADYEKHKVYACEVTHQGLSSPVTKSFNRGEC

-continued (Human IgG1 heavy chain DNA variant 1)

SEQ ID NO: 24 caagtgcaactggtggaatccggggccgaagtgaaaaagcccggagccactgtgaagatct cttgcaaagtgtccggctacaccttcaccgactattacatgcactgggtccagcaggcacc tgggaagggccttgagtggatgggtctggtcgatcccgaggacggcgaaactatctacgcc gagaagttccagggtcgcgtcaccatcaccgccgacacttccaccgacaccgcgtacatgg agctgtccagcttgaggtccgaggacacagccgtgtactactgcgccacggatgctcgggg aagcggcagctactacccgaaccacttcgactactggggacagggcactctcgtgactgtc tcgagcgcttctacaaagggcccctccgtgttcccgctcgctccatcatcgaagtctacca gcggaggcactgcggctctcggttgcctcgtgaaggactacttcccggagccggtgaccgt gtcgtggaacagcggagccctgaccagcggggtgcacacctttccggccgtcttgcagtca agcggcctttactccctgtcatcagtggtgactgtcccgtccagctcattgggaacccaaa cctacatctgcaatgtgaatcacaaacctagcaacaccaaggttgacaagaaagtcgagcc caaatcgtgtgacaagactcacacttgtccgccgtgcccggcacccgaactgctgggaggt cccagcgtctttctgttccctccaaagccaaagacacgctgatgatctcccgcaccccgg aggtcacttgcgtggtcgtggacgtgtcacatgaggacccagaggtgaagttcaattggta cgtggatggcgtcgaagtccacaatgccaaaactaagcccagagaagaacagtacaattcg acctaccgcgtcgtgtccgtgctcacggtgttgcatcaggattggctgaacgggaaggaat acaagtgcaaagtgtccaacaaggcgctgccggcaccgatcgagaaaactatctccaaagc gaagggacagcctagggaacctcaagtctacacgctgccaccatcacgggatgaactgact aagaatcaagtctcactgacttgtctggtgaaggggttttaccctagcgacattgccgtgg agtgggaatccaacggccagcagagaacaactacaagactaccccctccagtgctcgactc ggatggatcgttcttcctttactcgaagctcaccgtggataagtcccggtggcagcaggga aacgtgttctcctgctcggtgatgcatgaagccctccataaccactatacccaaaagtcgc tgtccctgtcgccgggaaag (Human IgG1 light chain DNA variant 1)

SEQ ID NO: 25 gacattgtgatgacccagtcccccgattcgcttgcggtgtccctgggagaacgggccacca ttaactgcaagagctcacagtccgtcctgtattcatcgaacaacaagaattacctcgcatg gtatcagcagaagcctggacagcctcccaagctgctcatctactgggctagcacccgcgaa tccggggtgccggatagattctccggatcgggttcgggcactgacttcactctgactatca actcactgcaagccgaggatgtcgcggtgtacttctgtcagcagtactacgacacccccgac ctttggacaaggcaccagactggagattaagcgtacggtggccgctcccctccgtgttcatc ttcccaccctccgacgagcagctgaagtccggcaccgcctccgtcgtgtgcctgctgaaca acttctaccccgcgaggccaaggtgcagtggaaggtggacaacgccctgcagtccggcaa ctcccaggaatccgtcaccgagcaggactccaaggacagcacctactccctgtcctccacc ctgaccctgtccaaggccgactacgagaagcacaaggtgtacgcctgcgaagtgacccacc agggcctgtccagccccgtgaccaagtccttcaaccggggcgagtgc (Human IgG4P heavy chain DNA variant 1)

SEQ ID NO: 26 caagtgcaactggtggaatccggggccgaagtgaaaaagcccggagccactgtgaagatct cttgcaaagtgtccggctacaccttcaccgactattacatgcactgggtccagcaggcacc tgggaagggccttgagtggatgggtctggtcgatcccgaggacggcgaaactatctacgcc gagaagttccagggtcgcgtcaccatcaccgccgacacttccaccgacaccgcgtacatgg -continued

```
agctgtccagcttgaggtccgaggacacagccgtgtactactgcgccacggatgctcgggg
aagcggcagctactacccgaaccacttcgactactggggacagggcactctcgtgactgtc
tcgagcgcttctacaaagggcccctccgtgttccctctggcccttgctcccggtccacct
ccgagtctaccgccgctctgggctgcctggtcaaggactacttccccgagcccgtgacagt
gtcctggaactctggcgccctgacctccggcgtgcacaccttcctgccgtgctgcagtcc
tccggcctgtactccctgtcctccgtcgtgaccgtgccctcctcagcctgggcaccaaga
cctacacctgtaacgtggaccacaagccctccaacaccaaggtggacaagcgggtggaatc
taagtacggccctccctgcccccctgccctgcccctgaatttctgggcggaccttccgtg
ttcctgttccccccaaagcccaaggacaccctgatgatctcccggaccccgaagtgacct
gcgtggtggtggacgtgtcccaggaagatcccgaggtccagttcaattggtacgtggacgg
cgtggaagtgcacaatgccaagaccaagcccagagaggaacagttcaactccacctaccgg
gtggtgtccgtgctgaccgtgctgcaccaggactggctgaacggcaaagagtacaagtgca
aggtgtccaacaagggcctgcccctccagcatcgaaaagaccatctccaaggccaagggcca
gccccgcgagcccaggtgtacaccctgccccctagccaggaagagatgaccaagaaccag
gtgtccctgacctgtctggtcaagggcttctaccctccgacattgccgtggaatgggagt
ccaacggccagcccgagaacaactacaagaccaccccccctgtgctggacagcgacggctc
cttcttcctgtactctcggctgaccgtggacaagtcccggtggcaggaaggcaacgtcttc
tcctgctccgtgatgcacgaggccctgcacaaccactacacccagaagtccctgtccctga
gcctgggcaag
```

(Human IgG4P light chain DNA variant 1)
SEQ ID NO: 27
```
gacattgtgatgacccagtcccccgattcgcttgcggtgtccctgggagaacgggccacca
ttaactgcaagagctcacagtccgtcctgtattcatcgaacaacaagaattacctcgcatg
gtatcagcagaagcctggacagcctcccaagctgctcatctactgggctagcacccgcgaa
tccggggtgccggatagattctccggatcgggttcgggcactgacttcactctgactatca
actcactgcaagccgaggatgtcgcggtgtacttctgtcagcagtactacgacacccccgac
cttttggacaaggcaccagactggagattaagcgtacggtggccgctcccctccgtgttcatc
ttcccacccctccgacgagcagctgaagtccggcaccgcctccgtcgtgtgcctgctgaaca
acttctaccccgcgaggccaaggtgcagtggaaggtggacaacgccctgcagtccggcaa
ctcccaggaatccgtcaccgagcaggactccaaggacagcacctactccctgtcctccacc
ctgaccctgtccaaggccgactacgagaagcacaaggtgtacgcctgcgaagtgacccacc
agggcctgtccagcccgtgaccaagtccttcaaccggggcgagtgc
```

(Mouse full length IgG1 heavy chain variant 2)
SEQ ID NO: 28
```
QVQLVQSGAEVKKPGATVKISCKVSGYTFTDYYMHWVQQAPGKGLEWMGLVDPEDGETIYA
EKFQGRVTITADTSTDTAYMELSSLRSEDTAVYYCATDARGSGSYYPNHFDYWGQGTLVTV
SSAKTTPPSVYPLAPGSAAQTNSMVTLGCLVKGYFPEPVTVTWNSGSLSSGVHTFPAVLQS
DLYTLSSSVTVPSSTWPSETVTCNVAHPASSTKVDKKIVPRDCGCKPCICTVPEVSSVFIF
PPKPKDVLTITLTPKVTCVVVDISKDDPEVQFSWFVDDVEVHTAQTQPREEQFNSTFRSVS
ELPIMHQDWLNGKEFKCRVNSAAFPAPIEKTISKTKGRPKAPQVYTIPPPKEQMAKDKVSL
TCMITDFFPEDITVEWQWNGQPAENYKNTQPIMDTDGSYFVYSKLNVQKSNWEAGNTFTCS
VLHEGLHNHHTEKSLSHSPGK
```

-continued (Mouse full length IgG1 light chain variant 2)
SEQ ID NO: 29
DIVMTQTPDSLAVSLGERATINCKSSQSVLYSSNNKNYLAWYQQKPGQPPKLLIYWASTRE

SGVPDRFSGSGSGTDFTLTINSLQAEDVAVYFCQQYYDTPTFGQGTRLEIKRTDAAPTVSI

FPPSSEQLTSGGASVVCFLNNFYPKDINVKWKIDGSERQNGVLNSWTDQDSKDSTYSMSST

LTLTKDEYERHNSYTCEATHKTSTSPIVKSFNRNEC (Human full length IgG1 heavy chain variant 1)
SEQ ID NO: 30
QVQLVESGAEVKKPGATVKISCKVSGYTFTDYYMHWVQQAPGKGLEWMGLVDPEDGETIYA

EKFQGRVTITADTSTDTAYMELSSLRSEDTAVYYCATDARGSGSYYPNHFDYWGQGTLVTV

SSASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYNS

TYRVVSVLTVLHQDWLNGKEYKCKVSNKALPAPIEKTISKAKGQPREPQVYTLPPSRDELT

KNQVSLTCLVKGFYPSDIAVEWESNGQPENNYKTTPPVLDSDGSFFLYSKLTVDKSRWQQG

NVFSCSVMHEALHNHYTQKSLSLSPGK (Human full length IgG1 light chain variant 1)
SEQ ID NO: 31
DIVMTQSPDSLAVSLGERATINCKSSQSVLYSSNNKNYLAWYQQKPGQPPKLLIYWASTRE

SGVPDRFSGSGSGTDFTLTINSLQAEDVAVYFCQQYYDTPTFGQGTRLEIKRTVAAPSVFI

FPPSDEQLKSGTASVVCLLNNFYPREAKVQWKVDNALQSGNSQESVTEQDSKDSTYSLSST

LTLSKADYEKHKVYACEVTHQGLSSPVTKSFNRGEC (Fab heavy chain variant 2)
SEQ ID NO: 32
QVQLVQSGAEVKKPGATVKISCKVSGYTFTDYYMHWVQQAPGKGLEWMGLVDPEDGETIYA

EKFQGRVTITADTSTDTAYMELSSLRSEDTAVYYCATDARGSGSYYPNHFDYWGQGTLVTV

SSASTKGPSVFPLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSC (Fab light chain variant 2)
SEQ ID NO: 33
DIVMTQTPDSLAVSLGERATINCKSSQSVLYSSNNKNYLAWYQQKPGQPPKLLIYWASTRE

SGVPDRFSGSGSGTDFTLTINSLQAEDVAVYFCQQYYDTPTFGQGTRLEIKRTVAAPSVFI

FPPSDEQLKSGTASVVCLLNNFYPREAKVQWKVDNALQSGNSQESVTEQDSKDSTYSLSST

LTLSKADYEKHKVYACEVTHQGLSSPVTKSFNRGEC (Human IgG4P heavy chain variant 2)
SEQ ID NO: 34
QVQLVQSGAEVKKPGATVKISCKVSGYTFTDYYMHWVQQAPGKGLEWMGLVDPEDGETIYA

EKFQGRVTITADTSTDTAYMELSSLRSEDTAVYYCATDARGSGSYYPNHFDYWGQGTLVTV

SSASTKGPSVFPLAPCSRSTSESTAALGCLVKDYFPEPVTVSWNSGALTSGVHTFPAVLQS

SGLYSLSSVVTVPSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTLPPSQEEMTKNQ

VSLTCLVKGFYPSDIAVEWESNGQPENNYKTTPPVLDSDGSFFLYSRLTVDKSRWQEGNVF

SCSVMHEALHNHYTQKSLSLSLGK (Human IgG4P light chain variant 2)
SEQ ID NO: 35
DIVMTQTPDSLAVSLGERATINCKSSQSVLYSSNNKNYLAWYQQKPGQPPKLLIYWASTRE

SGVPDRFSGSGSGTDFTLTINSLQAEDVAVYFCQQYYDTPTFGQGTRLEIKRTVAAPSVFI

-continued

```
FPPSDEQLKSGTASVVCLLNNFYPREAKVQWKVDNALQSGNSQESVTEQDSKDSTYSLSST

LTLSKADYEKHKVYACEVTHQGLSSPVTKSFNRGEC
```

REFERENCES

Bostrom, M. P. & Seigerman, D. A. (2005), HSS journal: The Musculoskeletal Journal of Hospital for Special Surgery 1, 9-18. The clinical use of allografts, demineralized bone matrices, synthetic bone graft substitutes and osteoinductive growth factors: a survey study.

Buza, J. A., 3rd & Einhorn, T. (2016), Clinical cases in mineral and bone metabolism: The Official Journal of the Italian Society of Osteoporosis, Mineral Metabolism, and Skeletal Diseases 13, 101-105. Bone healing in 2016.

Canalis, E., Parker, K. & Zanotti, S. (2012), J. Cell Physiol 227, 269-277. Gremlin1 is required for skeletal development and postnatal skeletal homeostasis.

Cho, T. J., Gerstenfeld, L. C. & Einhorn, T. A. (2002), Journal of Bone and Mineral Research: The Official Journal of the American Society for Bone and Mineral Research 17, 513-520. Differential temporal expression of members of the transforming growth factor beta superfamily during murine fracture healing.

Einhorn, T. A. & Gerstenfeld, L. C. (2015), Nat. Rev. Rheumatol. 11, 45-54. Fracture healing: mechanisms and interventions.

Ferguson, C., Alpern, E., Miclau, T. & Helms, J. A. (1999), Mechanisms of development 87, 57-66. Does adult fracture repair recapitulate embryonic skeletal formation-?Gazzerro, E. et al. (2005), Endocrinology 146, 655-665. Skeletal overexpression of gremlin impairs bone formation and causes osteopenia.

Gazzerro, E. et al. (2007), J. Biol. Chem. 282, 31549-31557. Conditional deletion of gremlin causes a transient increase in bone formation and bone mass.

Goulet, J. A., Senunas, L. E., DeSilva, G. L. & Greenfield, M. L. (1997), Clinical Orthopaedics and Related Research, 76-81. Autogenous iliac crest bone graft. Complications and functional assessment.

Hsu, D. R., Economides, A. N., Wang, X., Eimon, P. M. & Harland, R. M. (1998), Mol. Cell 1, 673-683. The Xenopus dorsalizing factor Gremlin identifies a novel family of secreted proteins that antagonize BMP activities.

Sato, K., Watanabe, Y., Harada, N., Abe, S., Matsushita, T., Yamanaka, K., Kaneko, T., & Sakai, Y. (2014) Tissue Eng Part C. Methods 20, 1037-1041.

Schmid, G. J., Kobayashi, C., Sandell, L. J. & Ornitz, D. M. (2009), Developmental Dynamics: An Official Publication of the American Association of Anatomists 238, 766-774. Fibroblast growth factor expression during skeletal fracture healing in mice.

Yu, Y. Y. et al. (2010), Bone 46, 841-851. Immunolocalization of BMPs, BMP antagonists, receptors, and effectors during fracture repair.

We claim:

1. A method for the treatment of a bone fracture or bone defect in a subject in need thereof comprising administering a therapeutically effective amount of an anti-gremlin-1 antibody or functionally active fragment, variant or derivative thereof to the subject, wherein the antibody or functionally active fragment, variant or derivative thereof comprises a heavy chain variable region comprising the sequence of SEQ ID NO: 3 or 4 for heavy chain complementarity determining region (HCDR) 1, the sequence of SEQ ID NO: 5 for HCDR2, and the sequence of SEQ ID NO: 6 for HCDR3, and a light chain variable region comprising the sequence of SEQ ID NO: 7 for light chain complementarity determining region (LCDR) 1, the sequence of SEQ ID NO: 8 for LCDR2, and the sequence of SEQ ID NO: 9 for LCDR3, wherein the bone fracture or bone defect is associated with a disease that affects bone integrity, and wherein the disease is rheumatoid arthritis.

2. The method according to claim 1, wherein the heavy chain variable region comprises a sequence having at least 95% identity to the sequence of SEQ ID NO: 10 and the light chain variable region comprises a sequence having at least 95% identity to the sequence of SEQ ID NO: 11.

3. The method according to claim 1, wherein the antibody comprises a heavy chain variable region (HCVR) of SEQ ID NO: 10 and/or a light chain variable region (LCVR) of SEQ ID NO: 11.

4. The method according to claim 1, wherein the functionally active antibody fragment is a Fab, Fab', F(ab')2, Fv or scFv.

* * * * *

SEQUENCE LISTING

```
Sequence total quantity: 35
SEQ ID NO: 1            moltype = AA  length = 184
FEATURE                 Location/Qualifiers
REGION                  1..184
                        note = recombinant sequence
source                  1..184
                        mol_type = protein
                        organism = synthetic construct
SEQUENCE: 1
MSRTAYTVGA LLLLLGTLLP AAEGKKKGSQ GAIPPPDKAQ HNDSEQTQSP QQPGSRNRGR  60
GQGRGTAMPG EEVLESSQEA LHVTERKYLK RDWCKTQPLK QTIHEEGCNS RTIINRFCYG 120
QCNSFYIPRH IRKEEGSFQS CSFCKPKKFT TMMVTLNCPE LQPPTKKKRV TRVKQCRCIS 180
IDLD                                                             184

SEQ ID NO: 2            moltype = AA  length = 139
FEATURE                 Location/Qualifiers
REGION                  1..139
                        note = recombinant sequence
source                  1..139
                        mol_type = protein
                        organism = synthetic construct
SEQUENCE: 2
MGSSHHHHHH SSGENLYFQG SAMPGEEVLE SSQEALHVTE RKYLKRDWCK TQPLKQTIHE  60
EGCNSRTIIN RFCYGQCNSF YIPRHIRKEE GSFQSCSFCK PKKFTTMMVT LNCPELQPPT 120
KKKRVTRVKQ CRCISIDLD                                             139

SEQ ID NO: 3            moltype = AA  length = 10
FEATURE                 Location/Qualifiers
REGION                  1..10
                        note = recombinant sequence
source                  1..10
                        mol_type = protein
                        organism = synthetic construct
SEQUENCE: 3
GYTFTDYYMH                                                        10

SEQ ID NO: 4            moltype = AA  length = 5
FEATURE                 Location/Qualifiers
```

```
REGION                    1..5
                          note = recombinant sequence
source                    1..5
                          mol_type = protein
                          organism = synthetic construct
SEQUENCE: 4
DYYMH                                                                     5

SEQ ID NO: 5              moltype = AA   length = 17
FEATURE                   Location/Qualifiers
REGION                    1..17
                          note = recombinant sequence
source                    1..17
                          mol_type = protein
                          organism = synthetic construct
SEQUENCE: 5
LVDPEDGETI YAEKFQG                                                       17

SEQ ID NO: 6              moltype = AA   length = 15
FEATURE                   Location/Qualifiers
REGION                    1..15
                          note = recombinant sequence
source                    1..15
                          mol_type = protein
                          organism = synthetic construct
SEQUENCE: 6
DARGSGSYYP NHFDY                                                         15

SEQ ID NO: 7              moltype = AA   length = 17
FEATURE                   Location/Qualifiers
REGION                    1..17
                          note = recombinant sequence
source                    1..17
                          mol_type = protein
                          organism = synthetic construct
SEQUENCE: 7
KSSQSVLYSS NNKNYLA                                                       17

SEQ ID NO: 8              moltype = AA   length = 7
FEATURE                   Location/Qualifiers
REGION                    1..7
                          note = recombinant sequence
source                    1..7
                          mol_type = protein
                          organism = synthetic construct
SEQUENCE: 8
WASTRES                                                                   7

SEQ ID NO: 9              moltype = AA   length = 8
FEATURE                   Location/Qualifiers
REGION                    1..8
                          note = recombinant sequence
source                    1..8
                          mol_type = protein
                          organism = synthetic construct
SEQUENCE: 9
QQYYDTPT                                                                  8

SEQ ID NO: 10             moltype = AA   length = 124
FEATURE                   Location/Qualifiers
REGION                    1..124
                          note = recombinant sequence
source                    1..124
                          mol_type = protein
                          organism = synthetic construct
SEQUENCE: 10
QVQLVESGAE VKKPGATVKI SCKVSGYTFT DYYMHWVQQA PGKGLEWMGL VDPEDGETIY         60
AEKFQGRVTI TADTSTDTAY MELSSLRSED TAVYYCATDA RGSGSYYPNH FDYWGQGTLV        120
TVSS                                                                    124

SEQ ID NO: 11             moltype = AA   length = 112
FEATURE                   Location/Qualifiers
REGION                    1..112
                          note = recombinant sequence
source                    1..112
                          mol_type = protein
                          organism = synthetic construct
SEQUENCE: 11
DIVMTQSPDS LAVSLGERAT INCKSSQSVL YSSNNKNYLA WYQQKPGQPP KLLIYWASTR         60
```

```
ESGVPDRFSG SGSGTDFTLT INSLQAEDVA VYFCQQYYDT PTFGQGTRLE IK          112

SEQ ID NO: 12              moltype = AA   length = 124
FEATURE                    Location/Qualifiers
REGION                     1..124
                           note = recombinant sequence
source                     1..124
                           mol_type = protein
                           organism = synthetic construct
SEQUENCE: 12
QVQLVQSGAE VKKPGATVKI SCKVSGYTFT DYYMHWVQQA PGKGLEWMGL VDPEDGETIY   60
AEKFQGRVTI TADTSTDTAY MELSSLRSED TAVYYCATDA RGSGSYYPNH FDYWGQGTLV  120
TVSS                                                              124

SEQ ID NO: 13              moltype = AA   length = 112
FEATURE                    Location/Qualifiers
REGION                     1..112
                           note = recombinant sequence
source                     1..112
                           mol_type = protein
                           organism = synthetic construct
SEQUENCE: 13
DIVMTQTPDS LAVSLGERAT INCKSSQSVL YSSNNKNYLA WYQQKPGQPP KLLIYWASTR   60
ESGVPDRFSG SGSGTDFTLT INSLQAEDVA VYFCQQYYDT PTFGQGTRLE IK          112

SEQ ID NO: 14              moltype = AA   length = 448
FEATURE                    Location/Qualifiers
REGION                     1..448
                           note = recombinant sequence
source                     1..448
                           mol_type = protein
                           organism = synthetic construct
SEQUENCE: 14
QVQLVESGAE VKKPGATVKI SCKVSGYTFT DYYMHWVQQA PGKGLEWMGL VDPEDGETIY   60
AEKFQGRVTI TADTSTDTAY MELSSLRSED TAVYYCATDA RGSGSYYPNH FDYWGQGTLV  120
TVSSAKTTPP SVYPLAPGSA AQTNSMVTLG CLVKGYFPEP VTVTWNSGSL SSGVHTFPAV  180
LQSDLYTLSS SVTVPSSTWP SETVTCNVAH PASSTKVDKK IVPRDCGCKP CICTVPEVSS  240
VPIFPPKPKD VLTITLTPKV TCVVVDISKD DPEVQFSWFV DDVEVHTAQT QPREEQFNST  300
FRSVSELPIM HQDWLNGKEF KCRVNSAAFP APIEKTISKT KGRPKAPQVY TIPPPKEQMA  360
KDKVSLTCMI TDFFPEDITV EWQWNGQPAE NYKNTQPIMD TDGSYFVYSK LNVQKSNWEA  420
GNTFTCSVLH EGLHNHHTEK SLSHSPGK                                    448

SEQ ID NO: 15              moltype = AA   length = 219
FEATURE                    Location/Qualifiers
REGION                     1..219
                           note = recombinant sequence
source                     1..219
                           mol_type = protein
                           organism = synthetic construct
SEQUENCE: 15
DIVMTQSPDS LAVSLGERAT INCKSSQSVL YSSNNKNYLA WYQQKPGQPP KLLIYWASTR   60
ESGVPDRFSG SGSGTDFTLT INSLQAEDVA VYFCQQYYDT PTFGQGTRLE IKRTDAAPTV  120
SIFPPSSEQL TSGGASVVCF LNNFYPKDIN VKWKIDGSER QNGVLNSWTD QDSKDSTYSM  180
SSTLTLTKDE YERHNSYTCE ATHKTSTSPI VKSFNRNEC                        219

SEQ ID NO: 16              moltype = AA   length = 454
FEATURE                    Location/Qualifiers
REGION                     1..454
                           note = recombinant sequence
source                     1..454
                           mol_type = protein
                           organism = synthetic construct
SEQUENCE: 16
QVQLVQSGAE VKKPGATVKI SCKVSGYTFT DYYMHWVQQA PGKGLEWMGL VDPEDGETIY   60
AEKFQGRVTI TADTSTDTAY MELSSLRSED TAVYYCATDA RGSGSYYPNH FDYWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSCDKT HTCPPCPAPE  240
LLGGPSVFLF PPKPKDTLMI SRTPEVTCVV VDVSHEDPEV KFNWYVDGVE VHNAKTKPRE  300
EQYNSTYRVV SVLTVLHQDW LNGKEYKCKV SNKALPAPIE KTISKAKGQP REPQVYTLPP  360
SRDELTKNQV SLTCLVKGFY PSDIAVEWES NGQPENNYKT TPPVLDSDGS FFLYSKLTVD  420
KSRWQQGNVF SCSVMHEALH NHYTQKSLSL SPGK                             454

SEQ ID NO: 17              moltype = AA   length = 219
FEATURE                    Location/Qualifiers
REGION                     1..219
                           note = recombinant sequence
source                     1..219
                           mol_type = protein
                           organism = synthetic construct
```

```
SEQUENCE: 17
DIVMTQTPDS LAVSLGERAT INCKSSQSVL YSSNNKNYLA WYQQKPGQPP KLLIYWASTR    60
ESGVPDRFSG SGSGTDFTLT INSLQAEDVA VYFCQQYYDT PTFGQGTRLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 18           moltype = AA  length = 227
FEATURE                 Location/Qualifiers
REGION                  1..227
                        note = recombinant sequence
source                  1..227
                        mol_type = protein
                        organism = synthetic construct
SEQUENCE: 18
QVQLVESGAE VKKPGATVKI SCKVSGYTFT DYYMHWVQQA PGKGLEWMGL VDPEDGETIY    60
AEKFQGRVTI TADTSTDTAY MELSSLRSED TAVYYCATDA RGSGSYYPNH FDYWGQGTLV   120
TVSSASTKGP SVFPLAPSSK STSGGTAALG CLVKDYFPEP VTVSWNSGAL TSGVHTFPAV   180
LQSSGLYSLS SVVTVPSSSL GTQTYICNVN HKPSNTKVDK KVEPKSC                 227

SEQ ID NO: 19           moltype = AA  length = 219
FEATURE                 Location/Qualifiers
REGION                  1..219
                        note = recombinant sequence
source                  1..219
                        mol_type = protein
                        organism = synthetic construct
SEQUENCE: 19
DIVMTQSPDS LAVSLGERAT INCKSSQSVL YSSNNKNYLA WYQQKPGQPP KLLIYWASTR    60
ESGVPDRFSG SGSGTDFTLT INSLQAEDVA VYFCQQYYDT PTFGQGTRLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 20           moltype = AA  length = 118
FEATURE                 Location/Qualifiers
REGION                  1..118
                        note = recombinant sequence
source                  1..118
                        mol_type = protein
                        organism = synthetic construct
SEQUENCE: 20
AMPGEEVLES SQEALHVTER KYLKRDWCKT QPLKQTIHEE GCNSRTIINR FCYGQCNSFY    60
IPRHIRKEEG SFQSCSFCKP KKFTTMMVTL NCPELQPPTK KKRVTRVKQC RCISIDLD     118

SEQ ID NO: 21           moltype = AA  length = 160
FEATURE                 Location/Qualifiers
REGION                  1..160
                        note = recombinant sequence
source                  1..160
                        mol_type = protein
                        organism = synthetic construct
SEQUENCE: 21
KKKGSQGAIP PPDKAQHNDS EQTQSPQQPG SRNRGRGQGR GTAMPGEEVL ESSQEALHVT    60
ERKYLKRDWC KTQPLKQTIH EEGCNSRTII NRFCYGQCNS FYIPRHIRKE EGSFQSCSFC   120
KPKKFTTMMV TLNCPELQPP TKKKRVTRVK QCRCISIDLD                         160

SEQ ID NO: 22           moltype = AA  length = 451
FEATURE                 Location/Qualifiers
REGION                  1..451
                        note = recombinant sequence
source                  1..451
                        mol_type = protein
                        organism = synthetic construct
SEQUENCE: 22
QVQLVESGAE VKKPGATVKI SCKVSGYTFT DYYMHWVQQA PGKGLEWMGL VDPEDGETIY    60
AEKFQGRVTI TADTSTDTAY MELSSLRSED TAVYYCATDA RGSGSYYPNH FDYWGQGTLV   120
TVSSASTKGP SVFPLAPCSR STSESTAALG CLVKDYFPEP VTVSWNSGAL TSGVHTFPAV   180
LQSSGLYSLS SVVTVPSSSL GTKTYTCNVD HKPSNTKVDK RVESKYGPPC PPCPAPEFLG   240
GPSVFLFPPK PKDTLMISRT PEVTCVVVDV SQEDPEVQFN WYVDGVEVHN AKTKPREEQF   300
NSTYRVVSVL TVLHQDWLNG KEYKCKVSNK GLPSSIEKTI SKAKGQPREP QVYTLPPSQE   360
EMTKNQVSLT CLVKGFYPSD IAVEWESNGQ PENNYKTTPP VLDSDGSFFL YSRLTVDKSR   420
WQEGNVFSCS VMHEALHNHY TQKSLSLSLG K                                  451

SEQ ID NO: 23           moltype = AA  length = 219
FEATURE                 Location/Qualifiers
REGION                  1..219
                        note = recombinant sequence
source                  1..219
                        mol_type = protein
                        organism = synthetic construct
```

```
SEQUENCE: 23
DIVMTQSPDS LAVSLGERAT INCKSSQSVL YSSNNKNYLA WYQQKPGQPP KLLIYWASTR    60
ESGVPDRFSG SGSGTDFTLT INSLQAEDVA VYFCQQYYDT PTFGQGTRLE IKRTVAAPSV   120
FIFPPSDEQL KSGTASVVCL LNNFYPREAK VQWKVDNALQ SGNSQESVTE QDSKDSTYSL   180
SSTLTLSKAD YEKHKVYACE VTHQGLSSPV TKSFNRGEC                          219

SEQ ID NO: 24           moltype = DNA   length = 1362
FEATURE                 Location/Qualifiers
misc_feature            1..1362
                        note = recombinant sequence
source                  1..1362
                        mol_type = other DNA
                        organism = synthetic construct
SEQUENCE: 24
caagtgcaac tggtggaatc cggggccgaa gtgaaaaagc ccggagccac tgtgaagatc    60
tcttgcaaag tgtccggcta caccttcacc gactattaca tgcactgggt ccagcaggca   120
cctgggaagg gccttgagtg gatgggtctg gtcgatcccg aggacggcga aactatctac   180
gccgagaagt tccagggtcg cgtcaccatc accgccgaca cttccaccga accgcgtac    240
atggagctgt ccagcttgag gtccgaggac acagccgtgt actactgcgc cacggatgct   300
cggggaagcg gcagctacta cccgaaccac ttcgactact ggggacaggg cactctcgtg   360
actgtctcga gcgcttctac aaagggcccc tccgtgttcc cgctcgctcc atcatcgaag   420
tctaccagcg gaggcactgc ggctctcggt tgcctcgtca aggactactt cccggagccg   480
gtgaccgtgt cgtggaacag cggagccctg accagcgggg tgcacacctt ccgcgccgtc   540
ttgcagtcaa gcgccttta ctccctgtca tcagtggtga ctgtcccgtc cagctcattg    600
ggaacccaaa cctacatctg caatgtgaat cacaaaccta gcaacaccaa ggttgacaag   660
aaagtcgagc ccaaatcgtg tgacaagact cacacttgtc ccgtgccc ggcaccgaa     720
ctgctgggag gtcccagcgt ctttctgttc cctccaaagc cgaaagaaca gctgatgatc   780
tcccgcaccc cggaggtcac ttgcgtggtc gtggacgtgt cacatgagga cccagaggtg   840
aagttcaatt ggtacgtgga tggcgtcgaa gtccacaatg ccaaaactaa gcccagagaa   900
gaacagtaca attcgaccta ccgcgtcgtg tccgtgctca cggtgttgca tcaggattgg   960
ctgaacggga aggaatacaa gtgcaaagtg tccaacaagg cgctgccggc accgatcgag  1020
aaaactatct ccaaagcgaa gggacagcct agggaacctc aagtctacac gctgccacca  1080
tcacgggatg aactgactaa gaatcaagtc tcactgactt gtctggtgaa ggggttttac  1140
cctagcgaca ttgccgtgga gtgggaatcc aacggcgac cagagaacaa ctacaagact  1200
accctctccag tgctcgactc ggatggatcg ttcttcctt actcgaagct caccgtggat  1260
aagtccggt ggcagcaggg aaacgtgttc tcctgctcgg tgatgcatga agccctccat   1320
aaccactata cccaaaagtc gctgtccctg tcgccgggaa ag                     1362

SEQ ID NO: 25           moltype = DNA   length = 657
FEATURE                 Location/Qualifiers
misc_feature            1..657
                        note = recombinant sequence
source                  1..657
                        mol_type = other DNA
                        organism = synthetic construct
SEQUENCE: 25
gacattgtga tgacccagtc ccccgattcg cttgcggtgt ccctgggaga acggggccacc   60
attaactgca agagctcaca gtccgtcctg tattcatcga acaacaagaa ttacctcgca   120
tggtatcagc agaagcctgg acagcctccc aagctgctca tctactgggc tagcacccgc   180
gaatccgggg tgcggatag attctccgga tcgggttcgg gcactgactt cactctgact    240
atcaactcac tgcaagccga ggatgtcgcg tgtactttct gtcagcagta ctacgacacc   300
ccgaccttttg acaaggcac cagactggag attaagcgta cggtggccgc tcccctcgtg   360
ttcatcttcc caccctccga cgagcagctg aagtccggca ccgcctccgt cgtgtgcctg   420
ctgaacaact tctaccccccg cgaggccaag gtgcagtgga aggtggacaa cgccctgcag   480
tccggcaact cccaggaatc cgtcaccgag caggactccaa aggacagcac ctactccctg   540
tcctccaccc tgaccctgtc caaggccgac tacgagaagc acaaggtgta cgcctgcgaa   600
gtgacccacc agggcctgtc cagccccgtg accaagtcct tcaaccgggg cgagtgc     657

SEQ ID NO: 26           moltype = DNA   length = 1353
FEATURE                 Location/Qualifiers
misc_feature            1..1353
                        note = recombinant sequence
source                  1..1353
                        mol_type = other DNA
                        organism = synthetic construct
SEQUENCE: 26
caagtgcaac tggtggaatc cggggccgaa gtgaaaaagc ccggagccac tgtgaagatc    60
tcttgcaaag tgtccggcta caccttcacc gactattaca tgcactgggt ccagcaggca   120
cctgggaagg gccttgagtg gatgggtctg gtcgatcccg aggacggcga aactatctac   180
gccgagaagt tccagggtcg cgtcaccatc accgccgaca cttccaccga accgcgtac    240
atggagctgt ccagcttgag gtccgaggac acagccgtgt actactgcgc cacggatgct   300
cggggaagcg gcagctacta cccgaaccac ttcgactact ggggacaggg cactctcgtg   360
actgtctcga gcgcttctac aaagggcccc tccgtgttcc ctctggcccc ttgctcccgg   420
tccacctccg agtctaccgc cgctctgggc tgcctcgtca aggactactt cccggagccg   480
gtgacagtgt cctggaactc tggcgccctg acctccggcg tgcacacctt cctgccgtg    540
ctgcagtcct ccggcctgta ctccctgtcc tccgtcgtga ccgtgccctc ctccagcctg   600
ggcaccaaga cctacacctg taacgtggac cacaagccct ccaacaccaa ggtggacaag   660
cgggtggaat ctaagtacgg ccctccctgc ccccctgcc ctgccctga tttctgggc      720
ggaccttccg tgttcctgtt ccccccaaag cccaaggaca cctgatgat ctcccggacc    780
```

```
                                         -continued
cccgaagtga cctgcgtggt ggtggacgtg tcccaggaag atcccgaggt ccagttcaat  840
tggtacgtgg acggcgtgga agtgcacaat gccaagacca gcccagaga ggaacagttc  900
aactccacct accgggtggt gtccgtgctg accgtgctgc accaggactg gctgaacggc  960
aaagagtaca agtgcaaggt gtccaacaag ggcctgccct ccagcatcga aaagaccatc 1020
tccaagggcc agccccgcga agccccaggt gtgtaccctg ccccc tagccaggaa 1080
gagatgacca gaaccaggt gtccctgacc tgtctggtca agggcttcta ccctcccgac 1140
attgccgtgg aatgggagtc caacggcag cccgagaaca actacaagac cccccccct 1200
gtgctggaca cgacggctc cttcttcctg tactctcggc tgaccgtgga caagtccgg 1260
tggcaggaag gcaacgtctt ctcctgctcc gtgatgcacg aggccctgca caaccactac 1320
acccagaagt ccctgtccct gagcctgggc aag                              1353

SEQ ID NO: 27           moltype = DNA   length = 657
FEATURE                 Location/Qualifiers
misc_feature            1..657
                        note = recombinant sequence
source                  1..657
                        mol_type = other DNA
                        organism = synthetic construct
SEQUENCE: 27
gacattgtga tgacccagtc ccccgattcg cttgcggtgt ccctgggaga acgggccacc  60
attaactgca gagctcaca gtccgtcctg tattcatcga acaacaagaa ttacctcgca 120
tggtatcagc agaagcctgg acagcctccc aagctgctca tctactgggc cagcacccgc 180
gaatccgggg tgccggatag attctccgga tcgggttcgg gcactgactt cactctgact 240
atcaactcac tgcaagccga ggatgtcgcg gtgtacttct gtcagcagta ctacgacacc 300
ccgacctttg gacaaggcac cagactggag attaagcgta cggtggccgc tcctccgtg  360
ttcatcttcc cacccctccga cgagcagctg aagtccggca ccgcctccgt cgtgtgcctg 420
ctgaacaact tctaccccg cgaggccaag gtgcagtgga aggtggacaa cgccctgcag 480
tccggcaact cccaggaatc cgtcaccgag caggactcca aggacagcac ctactccctg 540
tcctccaccc tgaccctgtc caaggccgac tacgagaagc acaaggtgta cgcctgcgaa 600
gtgacccacc agggcctgtc cagccccgtg accaagtcct tcaaccgggg cgagtgc    657

SEQ ID NO: 28           moltype = AA   length = 448
FEATURE                 Location/Qualifiers
REGION                  1..448
                        note = recombinant sequence
source                  1..448
                        mol_type = protein
                        organism = synthetic construct
SEQUENCE: 28
QVQLVQSGAE VKKPGATVKI SCKVSGYTFT DYYMHWVQQA PGKGLEWMGL VDPEDGETIY  60
AEKFQGRVTI TADTSTDTAY MELSSLRSED TAVYYCATDA RGSGSYYPNH FDYWGQGTLV 120
TVSSAKTTPP SVYPLAPGSA AQTNSMVTLG CLVKGYFPEP VTVTWNSGSL SSGVHTFPAV 180
LQSDLYTLSS SVTVPSSTWP SETVTCNVAH PASSTKVDKK IVPRDCGCKP CICTVPEVSS 240
VPIFPPKPKD VLTITLTPKV TCVVVDISKD DPEVQFSWFV DDVEVHTAQT QPREEQFNST 300
FRSVSELPIM HQDWLNGKEF KCRVNSAAFP APIEKTISKT KGRPKAPQVY TIPPPKEQMA 360
KDKVSLTCMI TDFFPEDITV EWQWNGQPAE NYKNTQPIMD TDGSYFVYSK LNVQKSNWEA 420
GNTFTCSVLH EGLHNHHTEK SLSHSPGK                                    448

SEQ ID NO: 29           moltype = AA   length = 219
FEATURE                 Location/Qualifiers
REGION                  1..219
                        note = recombinant sequence
source                  1..219
                        mol_type = protein
                        organism = synthetic construct
SEQUENCE: 29
DIVMTQTPDS LAVSLGERAT INCKSSQSVL YSSNNKNYLA WYQQKPGQPP KLLIYWASTR  60
ESGVPDRFSG SGSGTDFTLT INSLQAEDVA VYFCQQYYDT PTFGQGTRLE IKRTDAAPTV 120
SIFPPSSEQL TSGGASVVCF LNNFYPKDIN VKWKIDGSER QNGVLNSWTD QDSKDSTYSM 180
SSTLTLTKDE YERHNSYTCE ATHKTSTSPI VKSFNRNEC                        219

SEQ ID NO: 30           moltype = AA   length = 454
FEATURE                 Location/Qualifiers
REGION                  1..454
                        note = recombinant sequence
source                  1..454
                        mol_type = protein
                        organism = synthetic construct
SEQUENCE: 30
QVQLVESGAE VKKPGATVKI SCKVSGYTFT DYYMHWVQQA PGKGLEWMGL VDPEDGETIY  60
AEKFQGRVTI TADTSTDTAY MELSSLRSED TAVYYCATDA RGSGSYYPNH FDYWGQGTLV 120
TVSSASTKGP SVFPLAPSSK STSGGTAALG CLVKDYFPEP VTVSWNSGAL TSGVHTFPAV 180
LQSSGLYSLS SVVTVPSSSL GTQTYICNVN HKPSNTKVDK KVEPKSCDKT HTCPPCPAPE 240
LLGGPSVFLF PPKPKDTLMI SRTPEVTCVV VDVSHEDPEV KFNWYVDGVE VHNAKTKPRE 300
EQYNSTYRVV SVLTVLHQDW LNGKEYKCKV SNKALPAPIE KTISKAKGQP REPQVYTLPP 360
SRDELTKNQV SLTCLVKGFY PSDIAVEWES NGQPENNYKT TPPVLDSDGS FFLYSKLTVD 420
KSRWQQGNVF SCSVMHEALH NHYTQKSLSL SPGK                             454

SEQ ID NO: 31           moltype = AA   length = 219
```

```
FEATURE                 Location/Qualifiers
REGION                  1..219
                        note = recombinant sequence
source                  1..219
                        mol_type = protein
                        organism = synthetic construct
SEQUENCE: 31
DIVMTQSPDS LAVSLGERAT INCKSSQSVL YSSNNKNYLA WYQQKPGQPP KLLIYWASTR   60
ESGVPDRFSG SGSGTDFTLT INSLQAEDVA VYFCQQYYDT PTFGQGTRLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 32           moltype = AA  length = 227
FEATURE                 Location/Qualifiers
REGION                  1..227
                        note = recombinant sequence
source                  1..227
                        mol_type = protein
                        organism = synthetic construct
SEQUENCE: 32
QVQLVQSGAE VKKPGATVKI SCKVSGYTFT DYYMHWVQQA PGKGLEWMGL VDPEDGETIY   60
AEKFQGRVTI TADTSTDTAY MELSSLRSED TAVYYCATDA RGSGSYYPNH FDYWGQGTLV  120
TVSSASTKGP SVFPLAPSSK STSGGTAALG CLVKDYFPEP VTVSWNSGAL TSGVHTFPAV  180
LQSSGLYSLS SVVTVPSSSL GTQTYICNVN HKPSNTKVDK KVEPKSC                227

SEQ ID NO: 33           moltype = AA  length = 219
FEATURE                 Location/Qualifiers
REGION                  1..219
                        note = recombinant sequence
source                  1..219
                        mol_type = protein
                        organism = synthetic construct
SEQUENCE: 33
DIVMTQTPDS LAVSLGERAT INCKSSQSVL YSSNNKNYLA WYQQKPGQPP KLLIYWASTR   60
ESGVPDRFSG SGSGTDFTLT INSLQAEDVA VYFCQQYYDT PTFGQGTRLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 34           moltype = AA  length = 451
FEATURE                 Location/Qualifiers
REGION                  1..451
                        note = recombinant sequence
source                  1..451
                        mol_type = protein
                        organism = synthetic construct
SEQUENCE: 34
QVQLVQSGAE VKKPGATVKI SCKVSGYTFT DYYMHWVQQA PGKGLEWMGL VDPEDGETIY   60
AEKFQGRVTI TADTSTDTAY MELSSLRSED TAVYYCATDA RGSGSYYPNH FDYWGQGTLV  120
TVSSASTKGP SVFPLAPCSR STSESTAALG CLVKDYFPEP VTVSWNSGAL TSGVHTFPAV  180
LQSSGLYSLS SVVTVPSSSL GTKTYTCNVD HKPSNTKVDK RVESKYGPPC PPCPAPEFLG  240
GPSVFLFPPK PKDTLMISRT PEVTCVVVDV SQEDPEVQFN WYVDGVEVHN AKTKPREEQF  300
NSTYRVVSVL TVLHQDWLNG KEYKCKVSNK GLPSSIEKTI SKAKGQPREP QVYTLPPSQE  360
EMTKNQVSLT CLVKGFYPSD IAVEWESNGQ PENNYKTTPP VLDSDGSFFL YSRLTVDKSR  420
WQEGNVFSCS VMHEALHNHY TQKSLSLSLG K                                 451

SEQ ID NO: 35           moltype = AA  length = 219
FEATURE                 Location/Qualifiers
REGION                  1..219
                        note = recombinant sequence
source                  1..219
                        mol_type = protein
                        organism = synthetic construct
SEQUENCE: 35
DIVMTQTPDS LAVSLGERAT INCKSSQSVL YSSNNKNYLA WYQQKPGQPP KLLIYWASTR   60
ESGVPDRFSG SGSGTDFTLT INSLQAEDVA VYFCQQYYDT PTFGQGTRLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219
```